United States Patent
Tsai

(10) Patent No.: US 11,639,372 B1
(45) Date of Patent: May 2, 2023

(54) ZINC-CHARGED PEPTIDES FOR THE TREATMENT OF CANCER AND ALZHEIMER'S DISEASE

(71) Applicant: Men Hwei Tsai, Duarte, CA (US)

(72) Inventor: Men Hwei Tsai, Alhambra, CA (US)

(73) Assignee: Men Hwei Tsai, Duarte, CA (US)

( * ) Notice: Subject to any disclaimer, the term of this patent is extended or adjusted under 35 U.S.C. 154(b) by 0 days.

(21) Appl. No.: 17/544,773

(22) Filed: Dec. 7, 2021

(51) Int. Cl.
| | |
|---|---|
| *C07K 7/06* | (2006.01) |
| *C07K 14/47* | (2006.01) |
| *A61P 25/28* | (2006.01) |
| *A61K 47/18* | (2017.01) |
| *A61K 33/30* | (2006.01) |
| *A61P 35/00* | (2006.01) |
| *A61K 38/08* | (2019.01) |
| *C07K 4/12* | (2006.01) |

(52) U.S. Cl.
CPC .......... *C07K 14/4702* (2013.01); *A61K 33/30* (2013.01); *A61K 38/08* (2013.01); *A61K 47/183* (2013.01); *A61P 25/28* (2018.01); *A61P 35/00* (2018.01); *C07K 4/12* (2013.01); *C07K 7/06* (2013.01)

(58) Field of Classification Search
CPC .................. A61K 38/00; A61K 31/198; A61K 38/1709; A61K 35/20; A61K 38/018; A61K 38/38; A61K 9/1658; A61K 47/42; A61K 31/555; A61K 9/5169; A61K 2800/522; A23V 2002/00; A23V 2250/5424; A23V 2250/55; A23V 2250/1642; A23V 2250/54; C07K 14/47; C07K 16/18; C07K 14/765; C07K 14/76; A23L 33/19; A23L 33/17; A23L 33/18; A23L 2/66; A23L 27/66; C12N 9/00; G01N 33/68
See application file for complete search history.

(56) References Cited

U.S. PATENT DOCUMENTS

| | | | | |
|---|---|---|---|---|
| 11,371,037 | B1 * | 6/2022 | Tsai | C12N 9/94 |
| 2020/0009222 | A1 * | 1/2020 | Svanborg | C07K 14/705 |

OTHER PUBLICATIONS

Blakeborough et al. Zinc binding in cow's milk and human milk. Biochem. J. (1983) 209,505-512. (Year: 1983).*
Ren et al. a-Lactalbumin Possesses a Distinct Zinc Binding Site. J Biol Chem. Sep. 15, 1993;268(26):19292-8. (Year: 1993).*
Alpha-lactalbumin. NP_001371279.1 https://www.ncbi.nlm.nih.gov/protein/NP_001371279.1?report=genbank&log$=protalign&blast_rank=1&RID=DH3UXCYU013. downloaded Jul. 20, 2022. (Year: 2022).*
Lakatos et al. Histidine-rich branched peptides as Cu(II) and Zn(II) chelators with potential therapeutic application in Alzheimer's disease. Dalton Trans., 2012, 41, 1713. (Year: 2012).*
Samuel et al. Subclinical Mastitis in a European Multicenter Cohort: Prevalence, Impact on Human Milk (HM) Composition, and Association with Infant HM Intake and Growth. Nutrients 2020, 12, 105. (Year: 2020).*
Kreider, R. et al., Bioactive properties and clinical safety of a novel milk protein peptide, Nutrition Journal, 2011;10:99.
Robey, R.B. et al., Mitochondrial hexokinases, novel mediators of the antiapoptotic effects of growth factors and Akt, Oncogene, 2006, 25, 4683-4696, Published by 2006 Nature Publishing Group, doi:10.1038/sj.onc.1209595.
Mathupala, S. et al., Hexokinase-2 bound to mitochondria: Cancer's stygian link to the "Warburg effect" and a pivotal target for effective therapy, Semin Cancer Biol, Feb. 2009; 19(1): 17-24, doi:10.1016/j.semcancer.2008.11.006.

* cited by examiner

*Primary Examiner* — Aradhana Sasan
*Assistant Examiner* — Jia-Hai Lee
(74) *Attorney, Agent, or Firm* — Trojan Law Offices

(57) ABSTRACT

The present invention is generally directed to chemically synthesized peptides that are charged with zinc ions (herein "zinc-charged peptides"). The chemically synthesized peptides are based on the amino acid sequence of alpha-lactalbumin. The present invention is further directed to a method of preparing these two zinc-charged peptides by charging the chemically synthesized peptides with zinc ions. It is observed that charging these peptides with zinc ions activate the peptide's ability to induce apoptosis in cancer cell lines, as well as increase ATP, reduce Tau protein and inhibit P38 in the brain. The zinc-charged peptides are thus capable of treating cancer and diseases involving tauopathy such as Alzheimer's Disease. The present invention is thus further directed to a method of treating cancer and diseases involving tauopathy such as Alzheimer's Disease using the zinc-charged peptides.

10 Claims, 22 Drawing Sheets

Specification includes a Sequence Listing.

NECROPSY

Necropsy Findings:

| Tissue | Cont. #1 | Cont. #2 | Cont. #3 | Exp. #1 | Exp. #2 | Exp. #3 |
|---|---|---|---|---|---|---|
| Haircoat | N | N | N | N | N | N |
| Eyes | N | N | N | N | N | N |
| Ears | N | N | N | N | N | N |
| Nose | N | N | N | N | N | N |
| Mouth | N | N | N | N | N | N |
| Tail | N | N | N | N | N | N |
| Anus | N | N | N | N | N | N |
| Lungs | N | N | N | N | N | N |
| Heart | N | N | N | N | N | N |
| SQ tissue/fat | N | N | N | N | N | N |
| Liver/gall bladder | N | N | N | N | N | N |
| Intestines | N | N | N | N | N | N |
| Stomach | N | N | N | N | N | N |
| Pancreas | N | N | N | N | N | N |
| Spleen | N | N | N | N | N | N |
| Kidneys | N | N | N | N | N | N |
| Urinary bladder | N | N | N | N | N | N |
| Uterus/Ovaries | N | N | N | N | N | N |
| Weight (g) | 21.68 | 23.84 | 21.66 | 22.59 | 25.82 | 21.58 |

NE = Not examined  N = Normal  NA = Not applicable
FX = Fixed for histopath  AD = Additional diagnostics  AB = Abnormal

Comments: None

ZINC-CHARGED PEPTIDES FOR THE TREATMENT OF CANCER AND ALZHEIMER'S DISEASE

INCORPORATION BY REFERENCE OF SEQUENCE LISTING FILED VIA EFS-WEB

The content of the electronically submitted Sequence Listing (Name: 9042_SequenceListing.txt; Size: 693 bytes; Date Created: Dec. 7, 2021) filed with this application is hereby incorporated by reference in its entirety.

FIELD OF THE INVENTION

The present invention relates generally to zinc-charged peptides that induce apoptosis in cancer cells and cancer-associated fibroblasts, thereby treating cancer, as well as reduce Tau protein, inhibit P38 and increase ATP levels in the brain, thereby treating diseases involving tauopathy, such as Alzheimer's Disease and Parkinson's Disease.

BACKGROUND OF THE INVENTION

Cow milk is known to contain numerous proteins and other beneficial compounds for humans. In our previous study, when cow milk was treated with ethylenediaminetetraacetic acid (herein "EDTA") followed by zinc and papain enzyme incubation, this milk peptide mixture was found to contain bioactive peptides that are absorbed by gastrointestinal tract and show some physiological effects such as improvement of insulin sensitivity, neutrophil-to-lymphocyte ratio, and quality of life assessment of role of physical function on humans (Kreider et al, Nutrition Journal 2011, 10:99). In vitro, a cell culture study showed that this peptide mixture contained apoptosis-inducing activity on various cancer cell lines.

Since alpha-lactalbumin is the major milk protein present in milk, this protein was first tested to determine if the bioactive peptides were derived from alpha-Lactalbumin. Purified alpha-lactalbumin was therefore treated with EDTA and zinc acetate. This zinc-bound protein was found to contain apoptosis-inducing activity on various cancer cell lines. However, the zinc-bound alpha-lactalbumin was unable to be absorbed by gastrointestinal tract until it was enzymatically digested with papain. This finding suggested that the bioactive peptide mixture obtained from milk may be derived from alpha-lactalbumin.

To develop this protein as an anticancer agent, a smaller-sized protein that still contains apoptosis-inducing activity on cancer cells needed to be synthesized. This is based on the assumption that a small molecule is usually a better drug candidate than a large one. Thus, numerous series of peptides based on the amino acid sequence of alpha-lactalbumin were chemically synthesized.

To identify the bioactive peptides, a "peptide library" based on the amino acid sequence of alpha-lactalbumin was constructed. Peptides with lengths of 10 amino acids were chemically synthesized systematically starting from the N-terminal to the C-terminal ends of human alpha-lactalbumin. Once synthesized, each individual peptide was then treated with EDTA and zinc using the disclosed method and tested for its apoptosis-inducing activity on cancer cell lines, seeking a small-sized chemically synthesized peptide based on alpha-lactalbumin that is capable of inducing apoptosis on cancer cell lines.

SUMMARY OF THE INVENTION

The present invention is generally directed to two chemically synthesized peptides that are charged with zinc ions (herein "zinc-charged peptides"). The chemically synthesized peptides are based on the amino acid sequence of alpha-lactalbumin. The present invention is further directed to a method of preparing these two zinc-charged peptides starting from the two uncharged peptides.

The first peptide, listed as SEQ. ID NO. 1 in the accompanying sequence listing, has an amino acid sequence of E-Y-G-L-F-Q-I-S-N-K-L. This peptide, which is derived from natural human alpha-lactalbumin, will be referred to herein as "4H." The second peptide, listed as SEQ. ID NO. 2 in the accompanying sequence listing, is a more water-soluble version of 4H with a single amino acid change, and is an unnatural peptide. This peptide has an amino acid sequence of E-Y-G-L-F-Q-I-S-N-K-K and will be referred to herein as "4H3." Both these peptides were charged with zinc ions using the disclosed method to activate their apoptotic activities. Further, once these two peptides were charged with zinc ions, additional effects such as reducing Tau protein, increasing brain ATP levels and inhibiting P38 in the brain were observed, showing that these zinc-charged peptides further have a role in treating diseases involving tauopathy, such as Alzheimer's Disease and Parkinson's Disease.

Thus, it is an object of this invention to provide small-sized chemically synthesized peptides that have been charged with zinc, such that the zinc-charged peptides are capable of treating cancer by inducing apoptosis in cancer cells. It is a further object of this invention to provide small-sized chemically synthesized peptides that have been charged with zinc, such that the zinc-charged peptides are capable of treating diseases involving tauopathy, such as Alzheimer's Disease and Parkinson's Disease. It is a further object of this invention to provide a method for preparing zinc-charged peptides from uncharged chemically synthesized peptides such that the chemically synthesized peptides' properties for treating cancer and diseases involving tauopathy are activated.

Additionally, as the zinc-charged peptides have been shown to induce apoptosis in cancer-associated fibroblasts and cancer cells without affecting the normal cells, it is another object of this invention to provide a method of treating cancer using the zinc-charged peptides. Further, as the zinc-charged peptides have been shown to reduce Tau protein and increase ATP levels in the brain, it is another object of this invention to provide a method of treating diseases involving tauopathy, such as Alzheimer's Disease and Parkinson's Disease.

BRIEF DESCRIPTION OF THE DRAWINGS

These and other features and advantages of the present invention will become appreciated, as the same becomes better understood with reference to the specification, claims and drawings herein:

FIG. 19 is a table showing the results of a 28-day toxicology necropsy study of mice who were orally administered the zinc-charged peptide (4H3, 1 mg/mouse).

FIG. 20 is a table showing the results of a 28-day toxicology blood chemistry study of mice who were orally administered the zinc-charged peptide (4H3, 1 mg/mouse).

DETAILED DESCRIPTION OF THE INVENTION

Figure 1A:
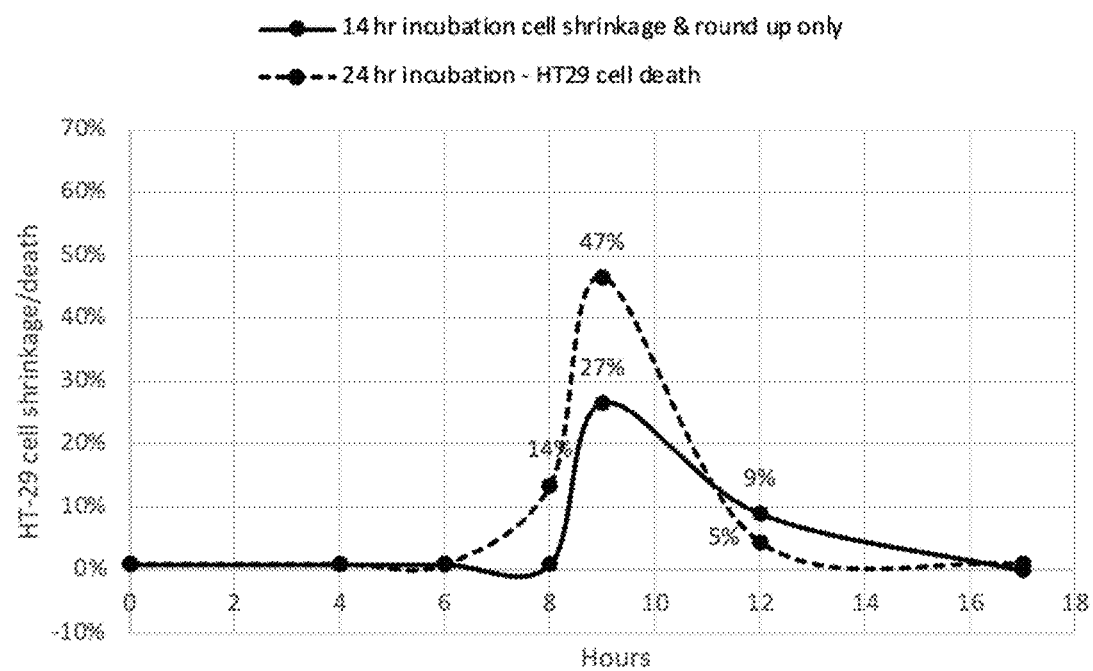
FIG. 1a is a line graph depicting the percent of cell shrinkage/death in HT-29 colon cancer cells after 14-hour and 24-hour incubation with saliva taken at various times from a human volunteer that had ingested 200 mg of the zinc-charged peptide 4H3 in liquid form.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

Disclosed herein are two zinc-charged chemically synthesized peptides based upon the alpha-lactalbumin that are able to treat cancer and diseases involving tauopathy once activated by the disclosed method of charging the peptides with zinc ions. The first peptide, 4H, has an amino acid sequence of E-Y-G-L-F-Q-I-S-N-K-L (Seq. No. 1). The second peptide, 4H3, has an amino acid sequence of E-Y-G-L-F-Q-I-S-N-K-K (Seq. No. 2). As shown, these peptides have identical amino acid sequences for the first 10 amino acids, with the last amino acid in the sequence differing for each peptide. The change in the last amino acid for 4H3 resulted in a more water-soluble version of the peptide than 4H. Prior to being charged with zinc ions, each of these peptides may be chemically synthesized using methods known in the art.

These peptides are based upon the amino acid sequence of purified alpha-lactalbumin. Both these peptides were charged with zinc ions using the disclosed method to activate their ability to treat cancer and diseases involving tauopathy, such as Parkinson's and Alzheimer's.

Method of Preparing the Zinc-Charged Peptides

As a preliminary matter, all disclosed methods of the zinc-charged peptides require a preliminary step of chemically synthesizing a peptide to be charged with zinc-ions. As discussed above, the preparation of these peptides may be accomplished by any preparation methods known in the art. Once this preliminary step is achieved, the peptides will be ready for treatment with zinc-ions using the disclosed method. Preferably, the peptides prepared will be the 4H peptide or the 4H3 peptide disclosed above.

A method of charging the peptides with zinc-ions, thereby preparing the zinc-charged peptides is disclosed. The general method of preparing the zinc-charged peptides includes (1) dissolving the peptide in a solvent, (2) incubating the dissolved peptide with a chelating agent, (3) incubating the mixture from step 2 with an excess of a zinc compound, which results in the peptide being charged with zinc ions, and (4) separating the zinc-charged peptide from the solution from step 3. In some embodiments, a fifth step of drying the zinc-charged peptide is also included. The separation in step 4 may be accomplished by dialyzing the solution with deionized water to help separate the zinc-charged peptides from the solution from step 3. Additionally, the optional drying in from step 5 may be accomplished by lyophilization. While dialysis and lyophilization are preferred methods for separating and drying the zinc-charged peptides, other methods of separating and drying the zinc-charged peptides may be used without departing from the concepts disclosed herein.

In the preferred embodiment, the peptides for the first step of the method are selected from either 4H or 4H3, having the amino acid sequences discussed above and disclosed by the sequence listing. Preferably, the preparation will begin with 1 millimolar (mM) of 4H or 4H3. In the preferred embodiment, the solvent will be selected from either deionized water or dimethyl sulfoxide ("DMSO"). Any quantity of solvent sufficient to dissolve all the peptide may be utilized. While these solvents are preferred, other solvents may be similarly used without departing from the concepts disclosed herein.

In a preferred embodiment, the chelating agent may be EDTA. In other embodiments, other chelating agents, including but not limited to dimercaprol, dimercaptosuccinic acid ("DMSA"), and egtazic acid ("EGTA"), may be utilized as the chelating agent without departing from the concepts disclosed herein. Preferably, the dissolved peptide will be incubated with 10 mM of EDTA for one hour.

In a preferred embodiment, the zinc compound is zinc acetate. In other embodiments, other zinc compounds, including but not limited to zinc oxide, zinc sulfate, and zinc nitrate, may be utilized. Any zinc compound may be used so long as the compound is capable of producing zinc ions to charge the peptides. Preferably, the resulting mixture from step 2 will be incubated with 50 mM zinc acetate for at least 8 hours.

A preferred embodiment of the above method includes the following steps: (1) dissolving 1 mM peptide in DMSO, (2) incubating the dissolved peptide with 10 mM EDTA for at least one hour; (3) incubating the resulting solution from step 1 with an excess quantity of zinc acetate for eight hours; and (4) separating the zinc-charged peptide from the resulting solution from step 3. The result will be a liquid formulation of the peptide that has been charged with zinc ions, thus resulting in the zinc-charged peptide. Should a solid dry formulation be desired, the following fifth step may be included: (5) drying the liquid formulation of the zinc-charged peptide by lyophilization. The amount of excess zinc acetate may be 50 mM in the preferred embodiment.

While other quantities and concentrations of peptide, the chelating agent, and zinc compound may be utilized with this method without departing from the concepts disclosed herein, it is critical to use an excess amount of the zinc compound to saturate all the EDTA that may be left over from the second step. Once the dissolved peptide is incubated with EDTA for at least an hour at step 2, the EDTA will have chelated all the surface ions off the peptide. At this point, most (if not all) of the EDTA in the mixture will have already reacted with the ions from the peptide. Thus, adding an excess of the zinc compound at step 3 causes any leftover EDTA to first react with the free zinc ions from the zinc compound until the EDTA is fully saturated in the mixture. Thus, the uncharged peptide is the only compound left in the solution to react with the remaining free zinc ions. Thus, due to the excess amount of the zinc compound, the remaining free zinc ions will react with the peptide in the solution, resulting in the zinc-charged peptides.

Therefore, the resulting mixture from the third step prior to separation will include zinc-charged peptides, EDTA that has been completely saturated by the peptide's surface ions and free zinc ions, and any leftover zinc compound. Therefore, the fourth step of separating the zinc-charged peptides from the leftover EDTA and zinc compound results in a liquid formulation of the zinc-charged peptide that may be then administered to a patient in need thereof. The optional fifth step will result in a dry powder version of the zinc-charged peptide should a dry powder version of the zinc-charged peptide be desired.

Biological Activities of the Zinc-Charged Peptides on Cancer

Figure 1B:
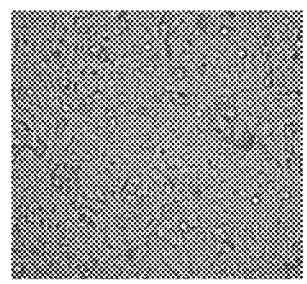
FIGS. 1B and 1c are slides depicting a duplicated experiment of HT-29 colon cancer cells incubated for 36 hours with control saliva samples without the zinc-charged peptide.
Figure 2:
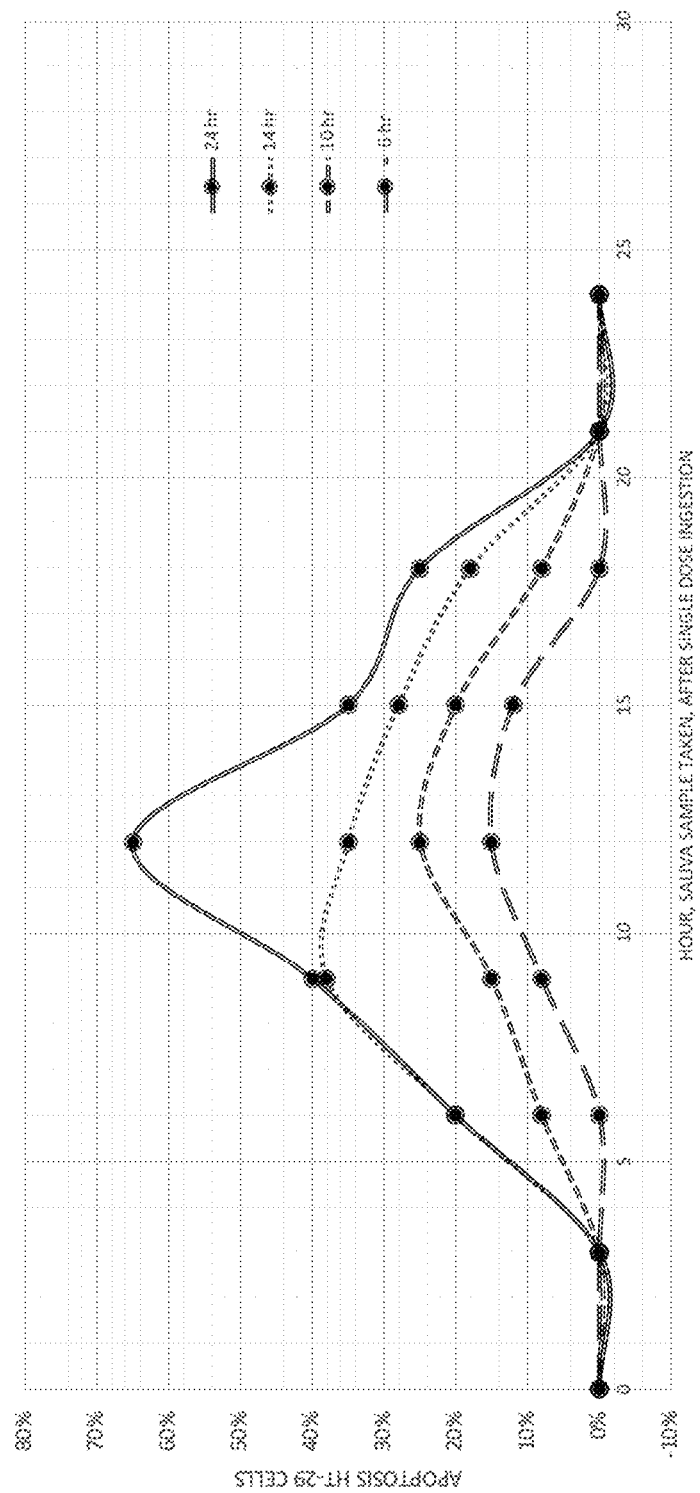
FIG. 2 is a line graph depicting the percent of apoptosis in HT-29 colon cancer cells after 6-hour, 10-hour, 14-hour and 24-hour incubation with saliva taken at various times from a human volunteer that had ingested 150 mg of zinc-charged peptide 4H3 in dry solid form.

It has been shown that the zinc-charged peptide induces apoptosis in various cancer lines. FIGS. 1a, 1b, and 2 show this effect of the zinc-charged peptide on the HT-29 cancer cell line after the zinc-charged peptide was given to a human volunteer. Specifically, 200 mg of zinc-charged 4H3 was orally given to the volunteer in a liquid form. The peptide mixture was an undialyzed sample, such that the zinc-charged 4H3 in the liquid had not yet been separated from the saturated EDTA and free zinc.

Saliva samples were then collected from the volunteer at 4-, 6-, 8-, 9-, 12- and 17-hours post-ingestion of the zinc-charged 4H3. The saliva samples were then incubated with HT-29 cancer cells for either 14-hours or 24-hours to observe the apoptotic effect. FIG. 1a depicts the percentage of cell shrinkage and death of HT-29 colon cancer cells after incubation for 14- and 24-hours with the human saliva samples containing the zinc-charged 4H3 noted above. As shown, the saliva sample collected 4-hours post-ingestion has little effect on the HT-29 cancer cells. However, in both the 14-hour and 24-hour incubations, the saliva sample collected 10-hours post-ingestion caused cell rounded up, cell shrinkage, and membrane blebbing, all signs of cells under apoptosis. In the 24-hour incubation sample, HT-29 cancer cell death was observed at 10-hours post-ingestion. The saliva-induced apoptotic activity thus peaked at 9-hours post-ingestion.

Figure 1C:
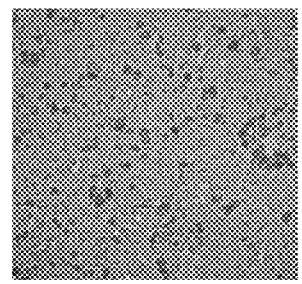
Figure 1D:
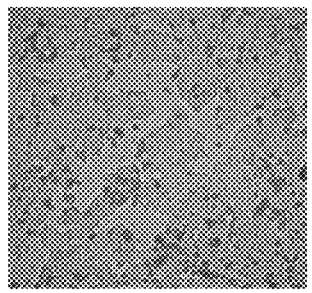
FIG. 1d is a slide depicting HT-29 colon cancer cells incubated for 36 hours with a saliva sample taken from a human volunteer 4-hours post-ingestion of the zinc-charged peptide 4H3.
Figure 1E:
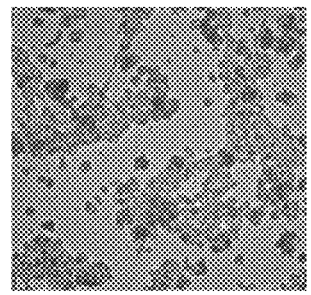
FIGS. 1e and 1f are slides depicting a duplicated experiment of HT-29 colon cancer cells incubated for 36 hours with saliva samples taken from a human volunteer 10-hours post-ingestion of the zinc-charged peptide 4H3.
Figure 1F:
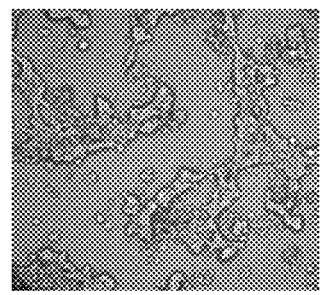

FIGS. 1B-f depicts microscopic slides of the HT-29 cancer cells after being incubated for 36 hours with specific saliva samples. FIGS. 1B and 1c depict a duplicative experiment utilizing the control saliva samples that do not have the zinc-charged 4H3. FIG. 1d depicts the saliva sample taken from the volunteer 4 hours after the zinc-charged peptide was ingested. FIGS. 1e and 1f depict saliva samples collected from the volunteer after 10-hour ingestion. As depicted in FIGS. 1B-1f, the control saliva samples did not show any apoptosis activity, while the saliva samples taken after 4-hour ingestion showed very little effect on the HT-29 cancer cells. However, the saliva samples collected after 10-hour ingestion depicted clear apoptosis activity, as the evidenced by the cell death observed in the two saliva samples shown in FIGS. 1e and 1f.

FIG. 2 depicts a dry, solid sample of the zinc-charged 4H3 that was administered to a human volunteer. Specifically, 150 mg of zinc-charged 4H3 was orally given to the volunteer in a dry solid form. This sample was dialyzed, dried down, and had arginine added as an absorption enhancer such that the dried powder included only the zinc-charged 4H3 and arginine. As with the test shown in FIG. 1a, the saliva samples were taken from the human subject 0-, 3-, 6-, 9-, 12-, 15-, 18-, 21-, and 24-hours post-ingestion. The saliva samples were then incubated with HT-29 cancer cells, and their apoptotic activity recorded after 6-, 10-, 14-, and 24-hours. As shown in FIG. 2, the saliva-induced apoptotic activity peaked at the 12$^{th}$ hour instead of the 9th hour for in the liquid formulation. This data corroborates that the zinc-charged peptides cause apoptotic activity in the HT-29 cancer cell lines, regardless of the chemical state the zinc-charged peptide was administered.

Figure 3A:
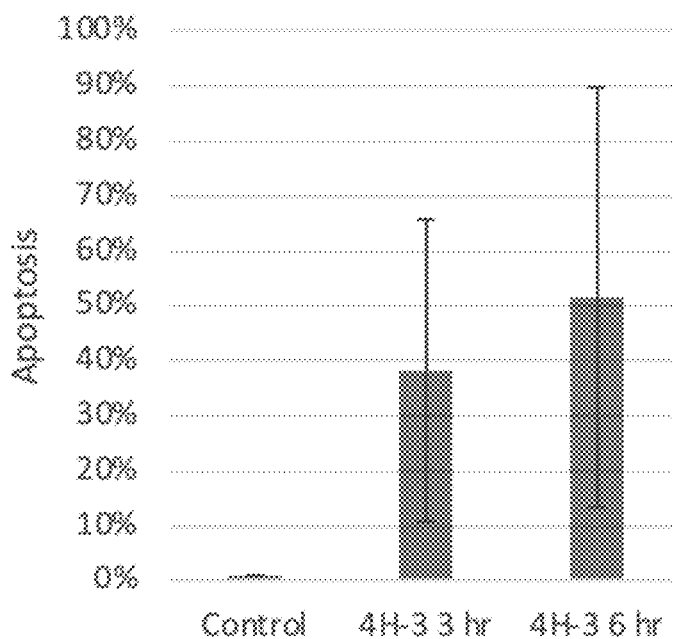
FIG. 3a is a bar graph depicting the apoptosis activity in HT-29 colon cancer cells incubated with pancreas homogenate extracted from mice given the zinc-charged peptide 4H3 for five days compared to a control.
Figure 3B:
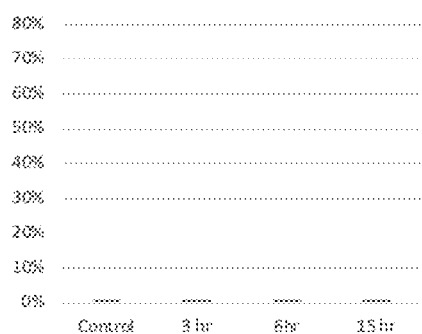
FIG. 3b is a bar graph depicting apoptosis activity in HT-29 colon cancer cells incubated with jaw homogenate extracted from mice given the zinc-charged peptide for five days compared to a control.
Figure 3C:
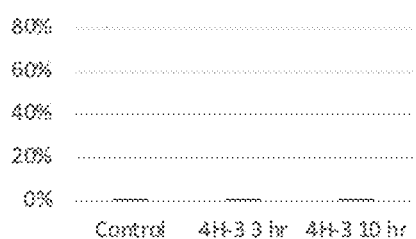
FIG. 3c is a bar graph depicting the apoptosis activity in HT-29 colon cancer cells incubated with colon homogenate extracted from mice given the zinc-charged peptide 4H3 for five days compared to a control.
Figure 3D:
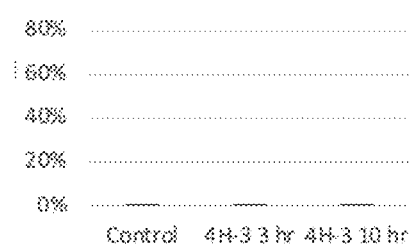
FIG. 3d is a bar graph depicting the apoptosis activity in HT-29 colon cancer cells incubated with lung homogenate extracted from mice given the zinc-charged peptide 4H3 for five days compared to a control.

When the zinc-charged peptide was given to mice, the protein extracts of pancreas tissue of these mice were found to contain apoptosis-inducing activity, suggesting that zinc-charged peptide is distributed to pancreas once it was absorbed into body. These observations were confirmed by studying the tissue distribution of the zinc-charged 4H3 in mice after five days administration, as shown in FIG. 3. For these tests, tissue homogenates were taken from the mice five days after receiving the zinc-charged 4H3, then prepared and incubated with HT-29 cancer cells for various times, followed by the determination of the percentage of cell under apoptosis. As shown in FIG. 3a, the homogenate prepared from the pancreas tissues contained apoptosis activity. However, those tissues from the jaw (FIG. 3b), colon (FIG. 3c), and lung (FIG. 3d) did not display any apoptosis activity. Thus, these observations show that zinc-charged peptides can be used as an anticancer agent for pancreatic cancer.

Figure 17A:
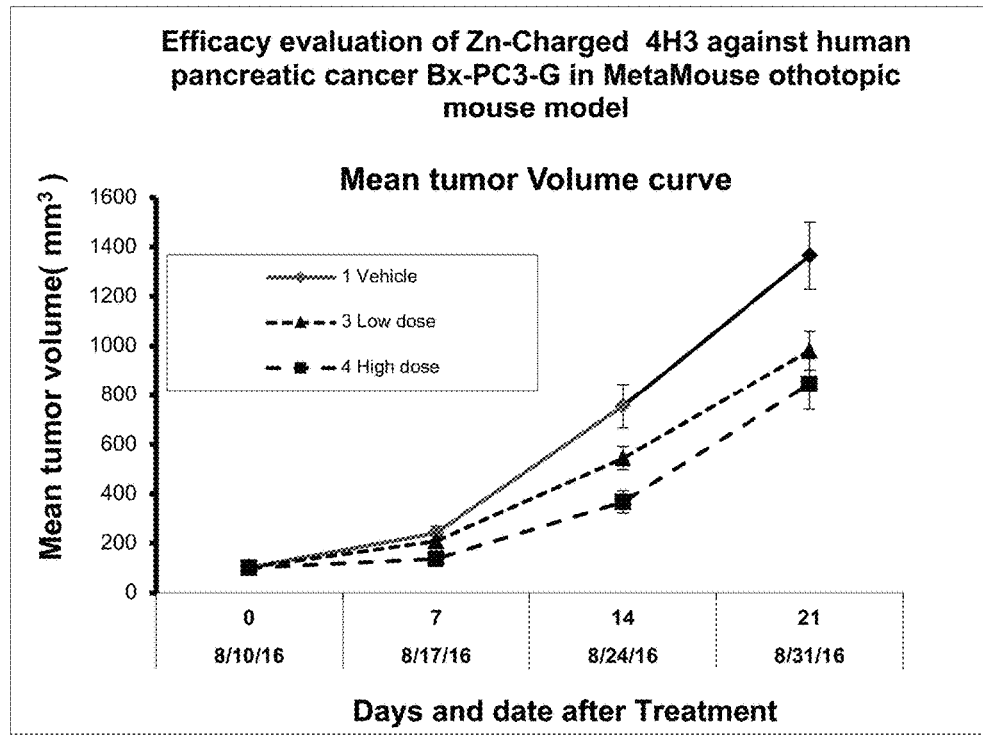
FIG. 17a is a line graph depicting the mean tumor volume of orthotopic pancreatic cancer tumors in mice over a 21-day period for a control, a low dose of the zinc-charged peptide (4H3, 0.5 mg/mouse), and a high dose of the zinc-charged peptide (4H3, 1.0 mg/mouse).
Figure 17B:
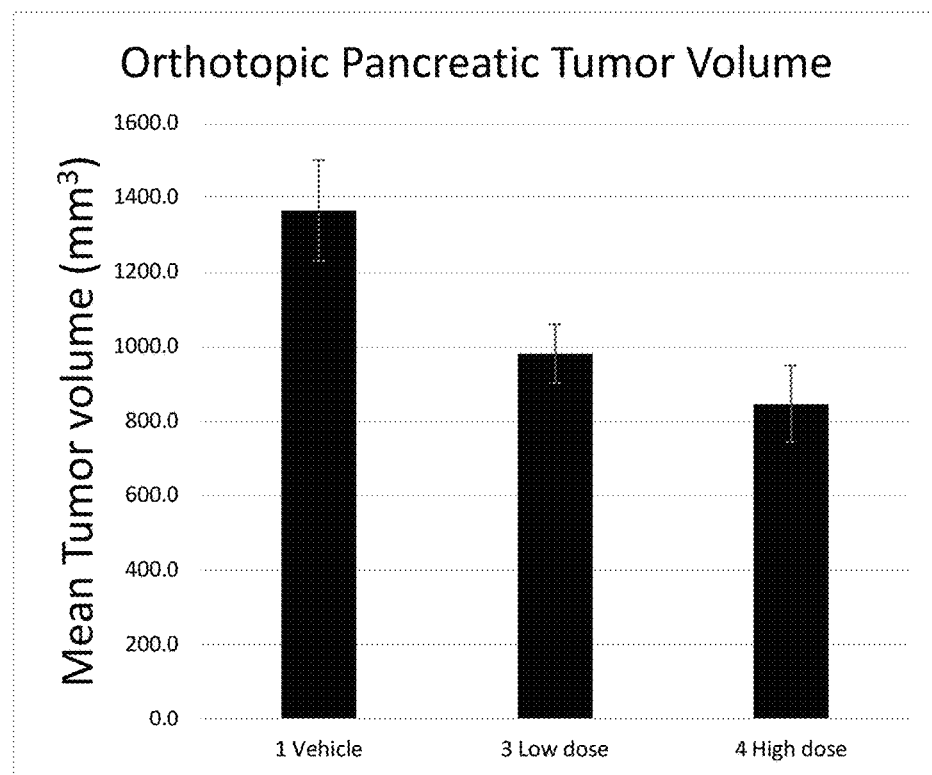
FIG. 17b is a bar graph depicting the mean tumor volume of orthotopic pancreatic cancer tumors in mice after a 21-day period for a control, a low dose of the zinc-charged peptide (4H3, 0.5 mg/mouse), and a high dose of the zinc-charged peptide (4H3, 1.0 mg/mouse).

Zinc-charged 4H3 was then tested on an orthotopic pancreatic cancer model in mice, the results of which are shown in FIG. 17. In this test, two doses of zinc-charged 4H3 and a control of only the vehicle were orally administered to mice with orthotopic pancreatic cancer. The zinc-charged 4H3 was administered in a "low dose" of 0.5 mg per mouse and a "high dose" of 1.0 mg per mouse. As shown in FIGS. 17a and 17b, it was found that zinc-charged 4H3 reduced mean tumor sizes by 28.1% and 38.0% respectively in a human pancreatic cancer Bx-PC3-G mouse orthotopic model. This data further verifies that the zinc-charged peptides can treat pancreatic cancer in patients by inducing apoptosis and reducing the growth of tumors in pancreatic cancer.

Figure 20:
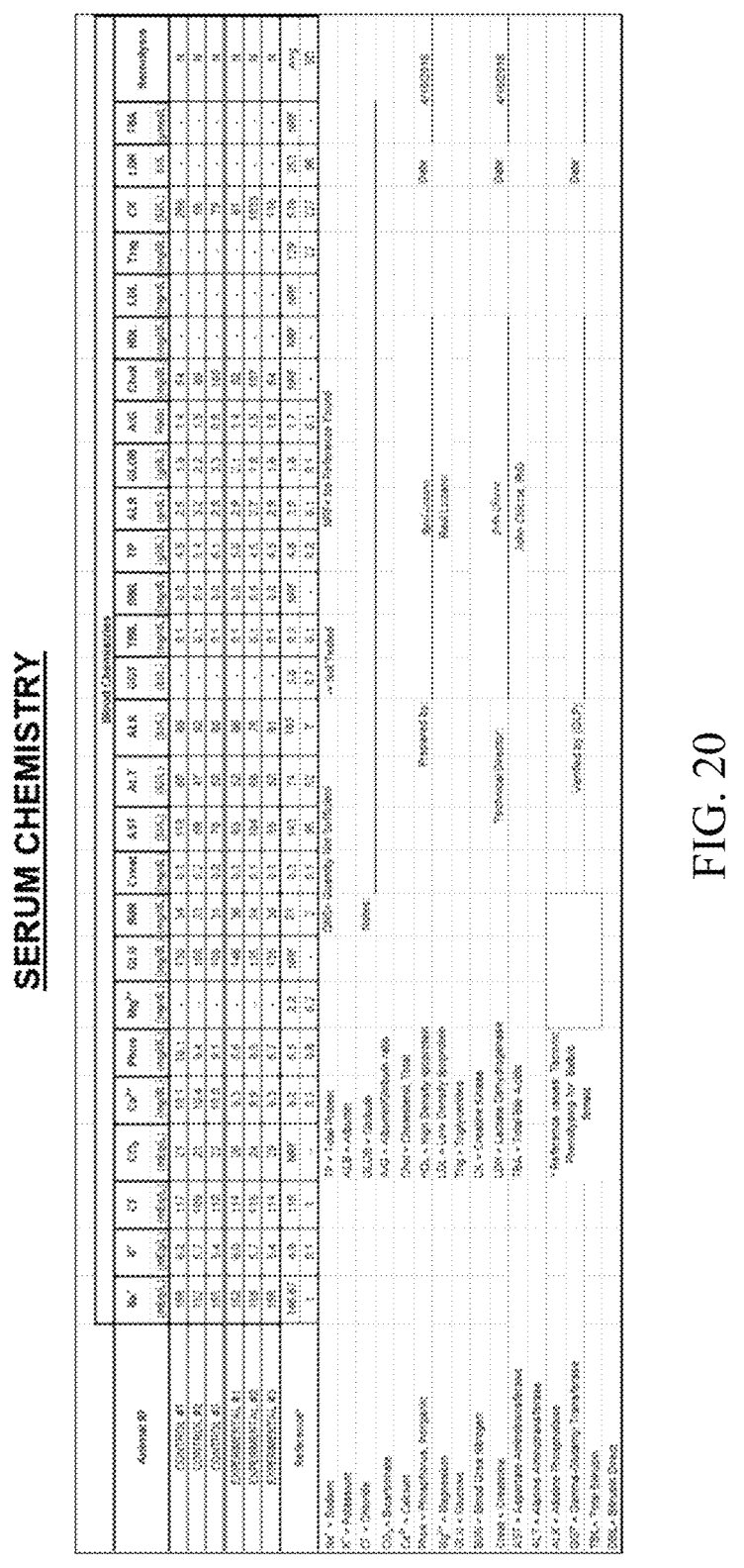

As shown in FIGS. 19-20, a 28-day toxicology study showed that the zinc-charged peptides caused no toxic or adverse effects on mice either in necropsy observation (FIG. 19) or on blood chemistry analyses (FIG. 20). This finding shows that the zinc-charged peptides should be safe for ingestion by humans, as the mice did not experience any toxic or adverse side effects. Pharmacokinetic studies showed that zinc-charged 4H3 has a half-life of 8 hours in serum.

Figure 18:
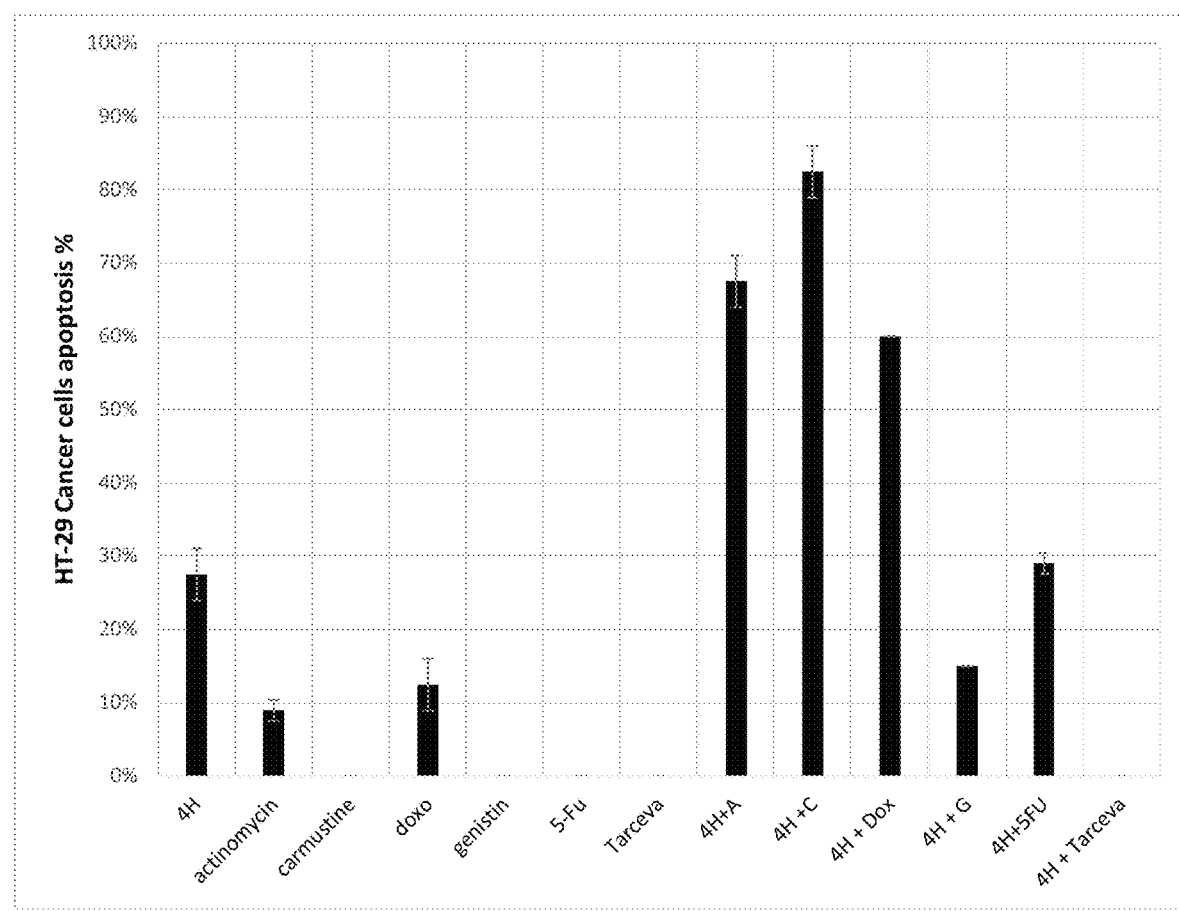
FIG. 18 is a bar graph comparing the apoptosis percentage in HT-29 cancer cells for the zinc-charged peptide (4H, 4 µM), other known chemotherapy drugs at 6 µg/mL), and combinations of the other known chemotherapy drugs and the zinc-charged peptide.

As shown in FIG. 18, the zinc-charged peptides are synergistic with several other chemotherapy agents. To test this, HT-29 colon cancer cells were pre-incubated with various chemotherapy drugs at 6 μg per ml for 12 hours, then zinc-charged 4H at 4 μM was added for an additional 6 hours. Most chemotherapy drugs take up to 48 hours to see substantial apoptosis, and as such, the cells were pre-incubated with chemotherapy drugs first. The chemotherapy drugs tested included actinomycin ("A"), carmustine ("C"), docorubicin ("Dox"), genistin ("G"), 5-FU, and Tarceva.

The results of this test are depicted in FIG. 18, which shows that the zinc-charged peptides are synergistic with chemotherapy drugs such as actinomycin, carmustine, doxorubicin, genistin and 5-FU. Once the zinc-charged 4H was added to each of these chemotherapy drugs, the percentage of apoptosis in HT-29 cancer cells was significantly increased. This shows that supplementing these chemotherapy treatments with the zinc-charged peptides will further aid in causing apoptosis in cancer cells.

As the above discussed testing demonstrated that the zinc-charged peptides were capable of inducing apoptosis in cancer cells, a mechanism of action was further studied to understand why the zinc-charged peptides induced apoptosis in cancer cells. To determine the mechanism of induction of apoptosis to HT-29 cancer cells by the zinc-charged peptides, a low concentration (1 μM) of zinc-charged 4H was incubated with HT-29 cancer cells, followed by biochemical analysis of the cell lysate of the HT-29 cancer cells.

Figure 4:
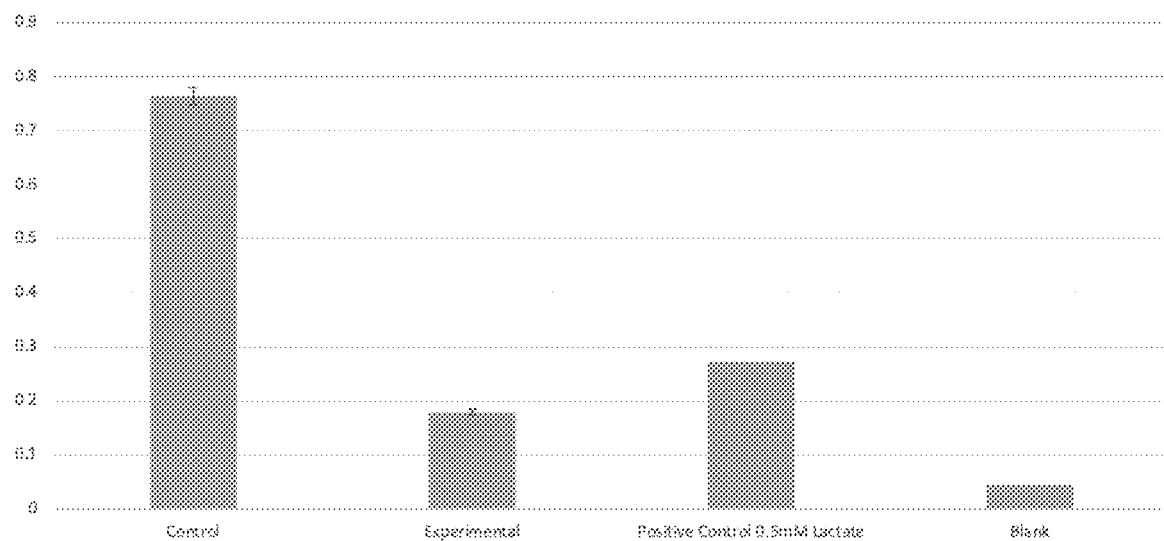
FIG. 4 is a bar graph depicting the level of glycolysis (lactate) in HT-29 cancer cells after being incubated with the zinc-charged peptide 4H.
Figure 5:
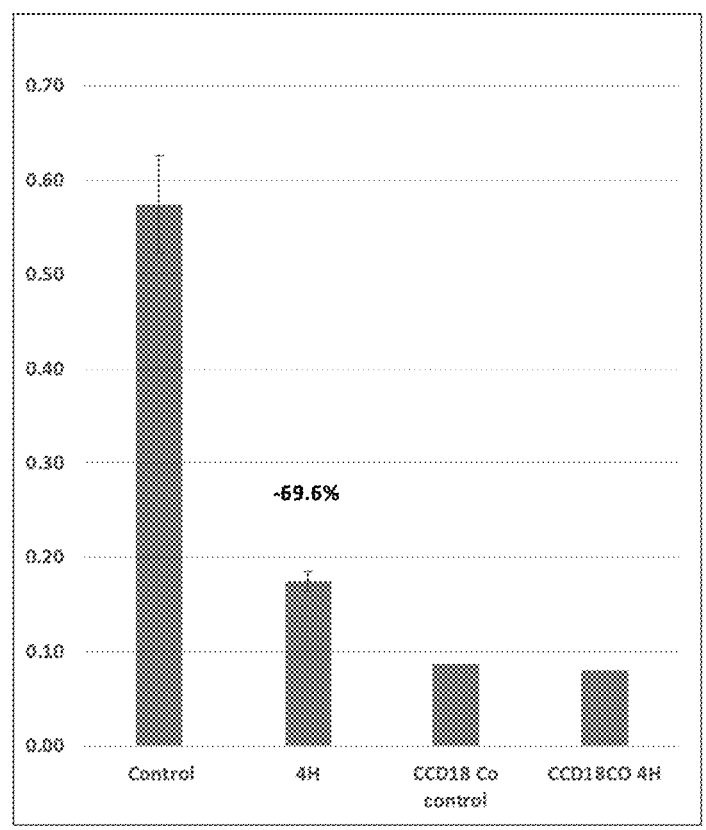
FIG. 5 is a bar graph depicting the level of cellular ATP in (1) a control of only the HT-29 cancer cells, (2) HT-29 cancer cells after being incubated with the zinc-charged peptide 4H, (3) normal colon cell line CCD18Co, and (4) normal colon cell line CCD18Co incubated with the zinc-charged peptide 4H.
Figure 6:
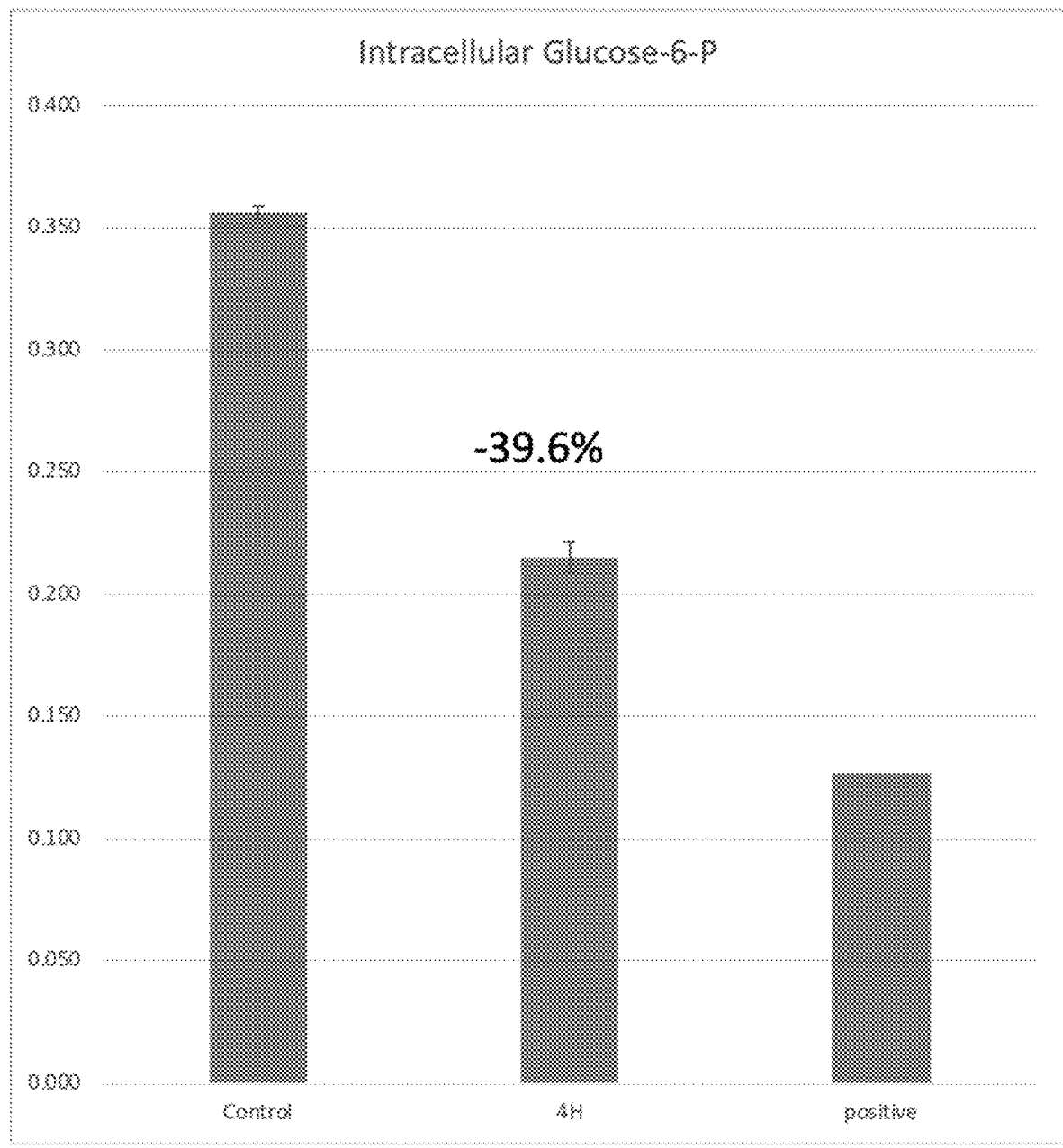
FIG. 6 is a bar graph depicting the level of intracellular Glucose phosphate in HT-29 cancer cells after being incubated with the zinc-charged peptide 4H compared with a control.

It was found that in the lysate of cells incubated with zinc-charged 4H, lactate, which is the end product of glycolysis, was 81.4% lower than the control cells, as shown in FIG. 4. Furthermore, the decreased lactate was associated with a lower ATP level and a lower Glucose-6-phosphate (G-6-P) level in HT-29 cells. FIG. 5 shows that the incubation with the zinc-charged peptides caused a significant decreased in cellular ATP level in HT-29 cancer cells but had no effects on normal colon cell line CCD18Co. FIG. 6 shows zinc-charged 4H reduced the intracellular G-6-P level by 39.6% after 6 hours of incubation. These results strongly suggested that the zinc-charged peptides may inhibit glycolysis at the hexokinase II enzyme level, which is the first enzyme used in glycolysis.

Figure 7:
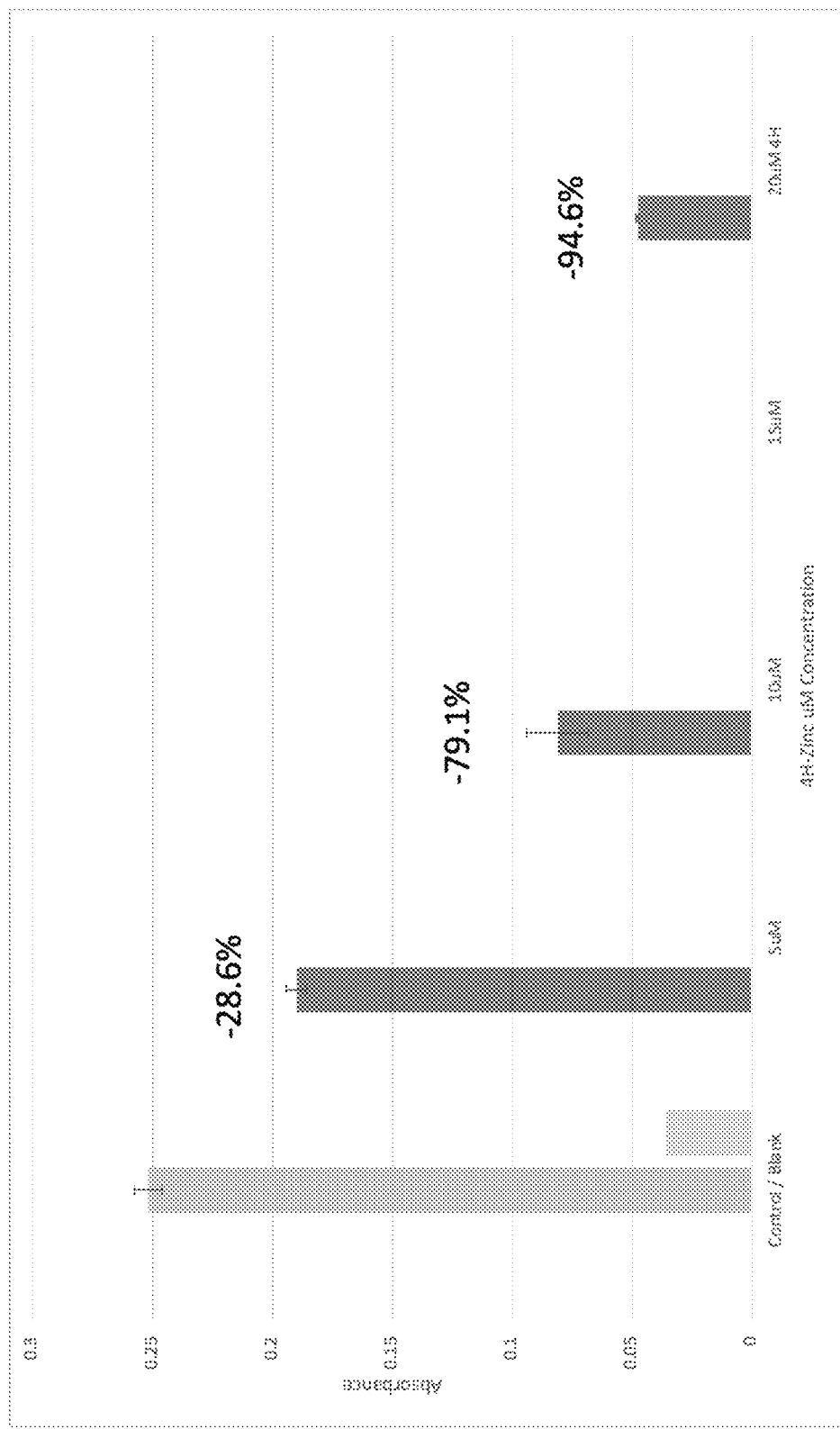
FIG. 7 is a bar graph depicting an in vitro hexokinase II assay showing the percent inhibition of hexokinase II by various concentrations of the zinc-charged peptide 4H.

To test confirm that the zinc-charged peptides inhibit hexokinase II resulting in the inhibition of glycolysis, an in vitro hexokinase II assay was performed. FIG. 7 depicts the results of the in vitro hexokinase II assay. In this test, it was observed that hexokinase II was inhibited by zinc-charged 4H in a dose-dependent manner. Specifically, at 5 μM of the zinc-charged 4H, hexokinase II was inhibited 28.6%. At 10 μM of the zinc-charged 4H, hexokinase II was inhibited 79.1%. Lastly, at 20 μM of the zinc-charged 4H, hexokinase II was inhibited 94.6%. These findings confirm that the zinc-charged peptides inhibit glycolysis at the hexokinase II enzyme level.

Figure 8A:
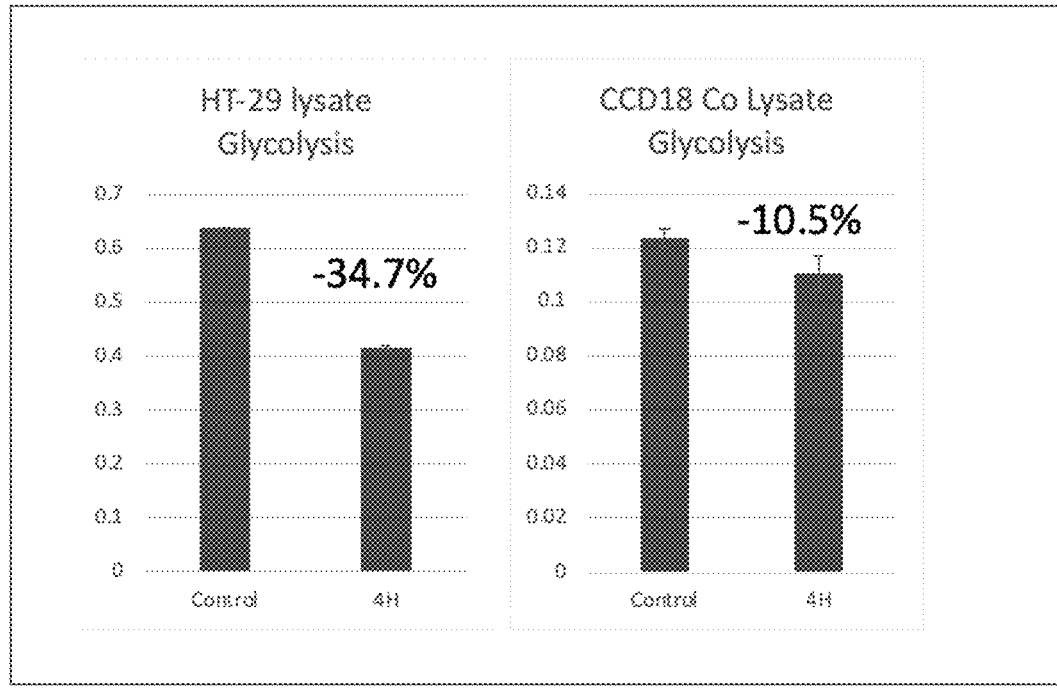
FIG. 8a is a bar graph depicting the level of glycolysis end product lactate in HT-29 colon cancer cell lysate and of normal CCD18Co colon cell lysate after incubation with zinc-charged peptide 4H compared to a control of unincubated HT-29 cancer cell lysate and unincubated normal CCD18Co colon cell lysate.
Figure 8B:
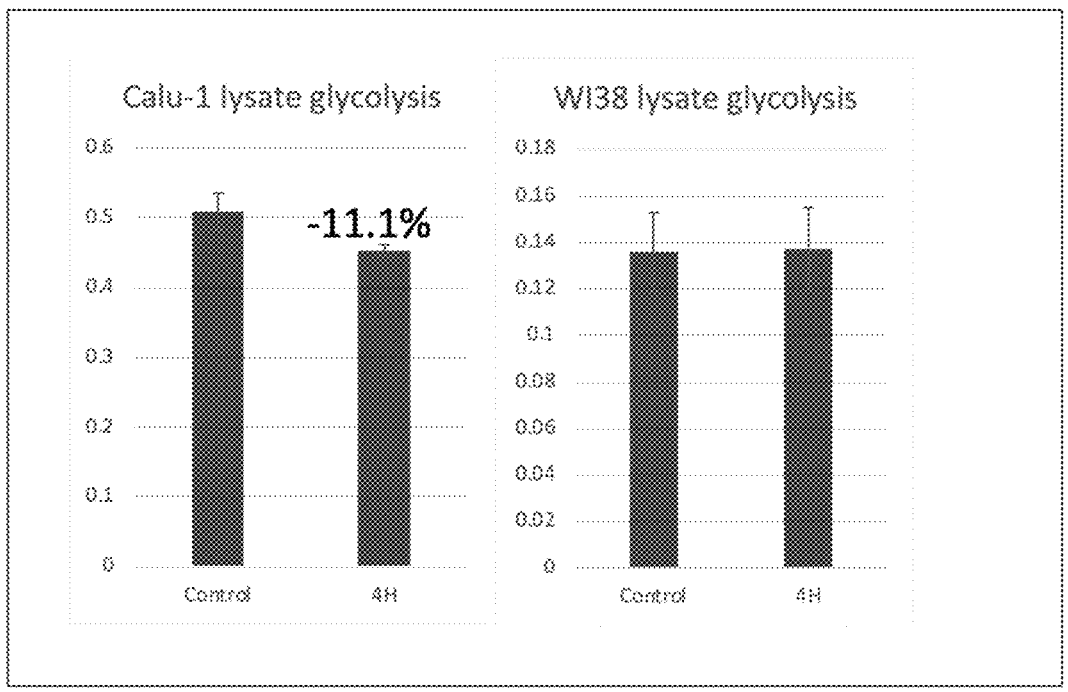
FIG. 8b is a bar graph depicting the level of glycolysis end product lactate in Calu-1 lung cancer cell lysate and of normal WI38 lung cell lysate after incubation with zinc-charged peptide 4H compared to a control of unincubated Calu-1 lung cancer cell lysate and unincubated normal WI38 lung cell lysate.

Interestingly, it was observed that normal cell lines are less impacted by the zinc-charged peptides' ability to inhibit glycolysis. As shown in FIG. 8a, while zinc-charged 4H inhibited glycolysis in HT-29 colon cancer cells by up to 34.7%, the normal colon cell line CCD18Co was only inhibited 10.5%. The zinc-charged peptides ability to inhibit glycolysis in other cancer cell lines, such as lung cancer, compared to their normal counterparts was also tested. As shown in FIG. 8b, Calu-1 lung cancer cells were inhibited 11.1%, while the normal WI38 lung cells were not affected, showing 0% inhibition.

Figure 9A:
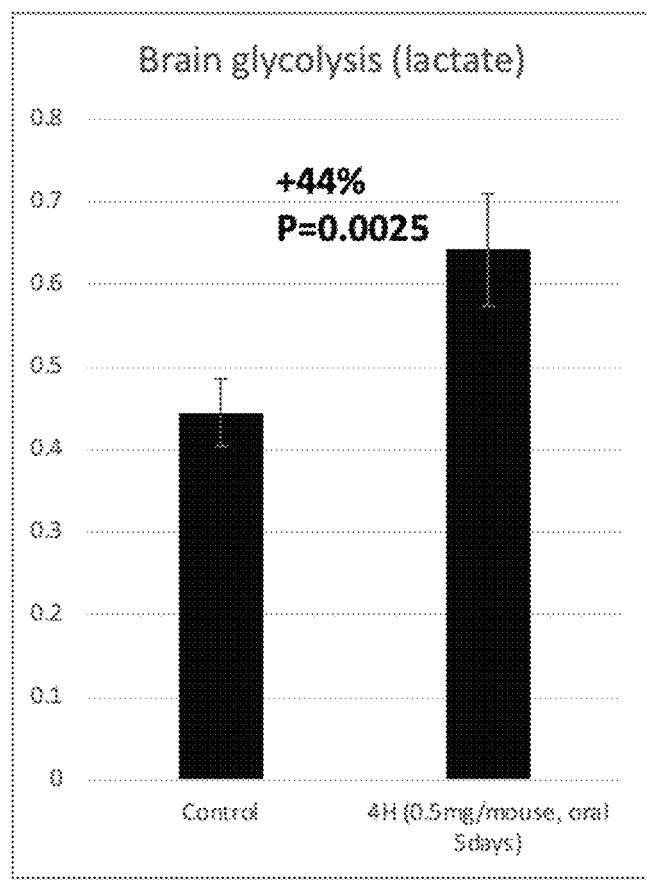
FIG. 9a is a bar graph depicting the level of glycolysis in the brain tissue of normal mice (N=4) after the mice were orally administered the zinc-charged peptide (4H, 0.5 mg/mouse) for five days compared to a control.
Figure 9B:
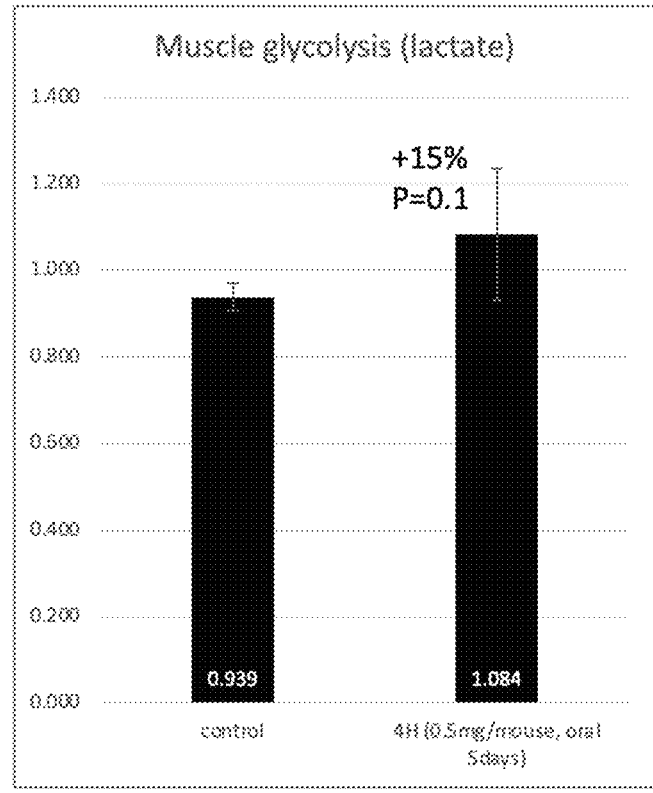
FIG. 9b is a bar graph depicting the level of glycolysis in the muscle tissue of normal mice after the mice were orally administered the zinc-charged peptide (4H, 0.5 mg/mouse) for five days compared to a control.

To further study this observed phenomena in vivo, normal mice were fed with the zinc-charged 4H for five days, and the glycolysis of normal brain cells were studied. FIG. 9 depicts the results of this study. For this study, two groups of mice having four mice per group were compared, one being the control and the other being fed 0.5 mg of zinc-charged 4H per mouse per day for 5 days orally. After 5 days, brain and muscle tissue was collected, homogenized, and assayed for glycolysis rate.

Figure 10:
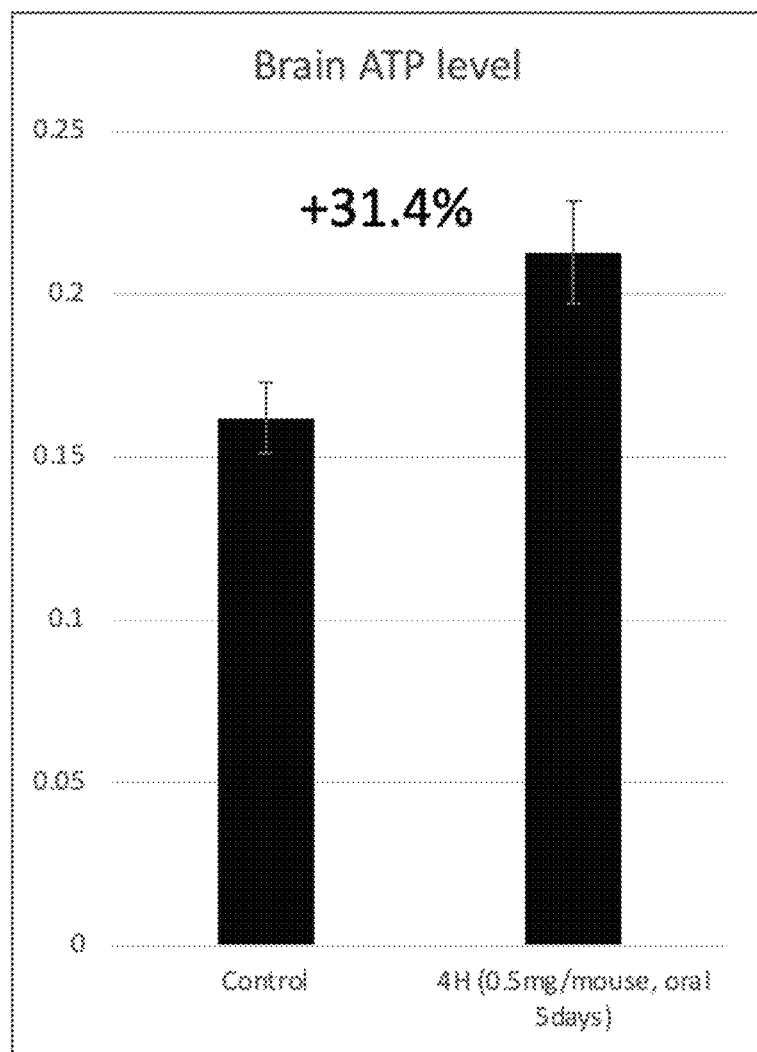
FIG. 10 is a bar graph depicting the brain ATP level of normal mice after the mice were orally administered the zinc-charged peptide (4H, 0.5 mg/mouse) for five days compared to a control.

In mice fed with 0.5 mg of zinc-charged 4H for 5 days, the brain glycolysis of these mice was enhanced by 44%. The glycolysis of muscle of these mice was also slightly increased by 15%. As shown in FIG. 10, the increase in brain glycolysis in these mice was accompanied with a 31.4% increase in brain ATP level. This result further supports that finding that zinc-charged peptides enhance glycolysis in the brain of normal mice.

It was also observed that the zinc-charged peptides caused ATP depletion and hexokinase II inhibition in cancer-associated fibroblasts. Cancer-associated fibroblasts ("CAFs") are a group of cells present in the surroundings of cancer. It is known that cancer has an ability to influent the surrounding cells to make them providing nutrients to cancer. During testing on different cell types whose glycolysis can be inhibited by the zinc-charged peptides, it was observed that the glycolysis of cancer-associated fibroblasts were also inhibited by the zinc-charged peptides.

Figure 12A:
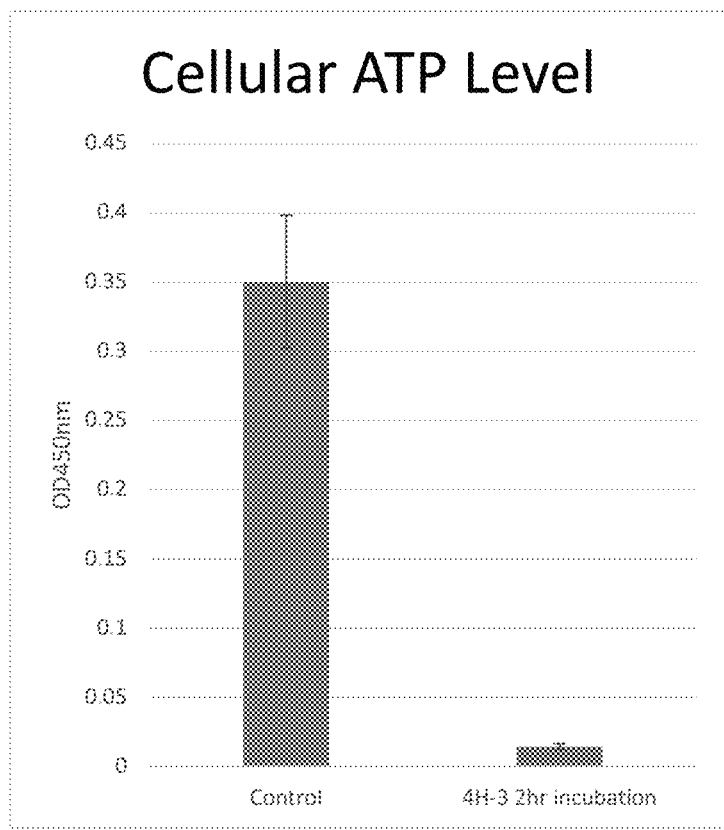
FIG. 12a is a bar graph depicting the level of cellular ATP in cancer-associated fibroblasts after being treated with the zinc-charged peptide (4H3, 2 µM, for 2 hours) compared to a control.
Figure 12B:
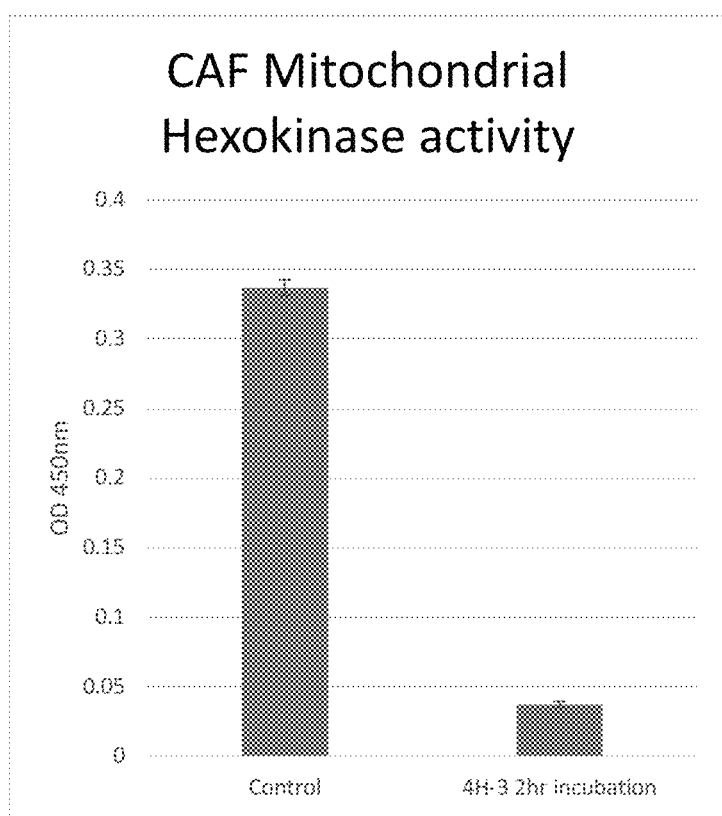
FIG. 12b is a bar graph depicting the level of mitochondrial hexokinase II activity in cancer-associated fibroblasts after being treated with the zinc-charged peptide (4H3, 2 µM, for 2 hours) compared to a control.

FIGS. 12a-b display a cell culture study showing the ATP levels and hexokinase II activities of CAFs that were cultured with 2 µM zinc-charged 4H3 for 2 hours. It was found that ATP levels of these CAFs were reduced by 95.6%, whereas hexokinase II activity was reduced by 88.9%. These findings confirmed that the zinc-charged peptides caused ATP depletion and hexokinase II inhibition in CAFs.

Figure 13A:
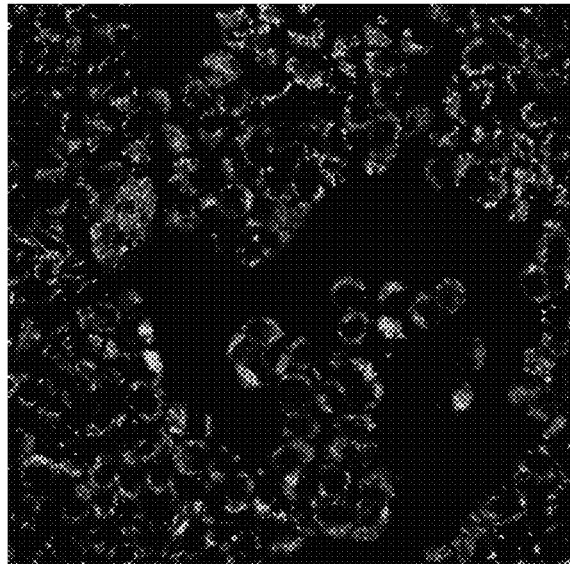
FIG. 13a is a slide depicting the location of the zinc-charged peptide in HT-29 cancer cells by staining the zinc-charged peptide with a fluorescence dye marker.
Figure 13B:
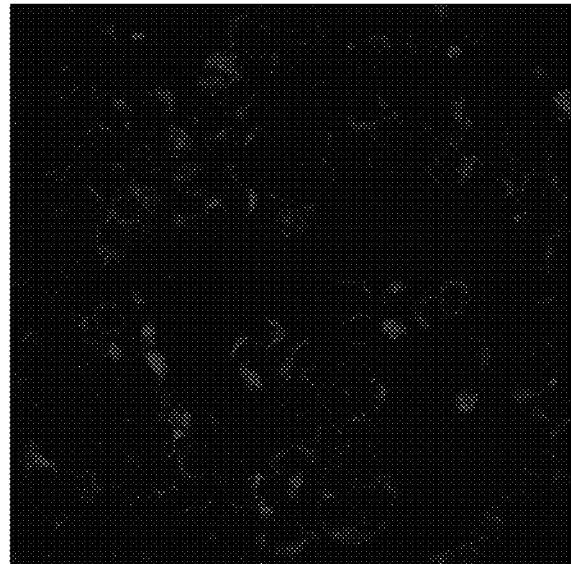
FIG. 13b is a slide depicting the location of the mitochondria in HT-29 cancer cells by staining the mitochondria with a fluorescence dye marker.
Figure 13C:
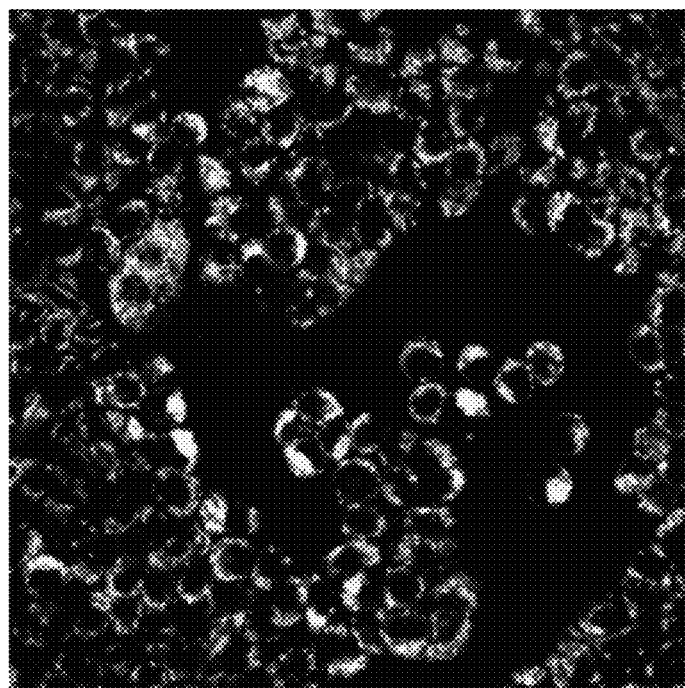
FIG. 13c is a slide depicting the overlapped composite of FIGS. 13a and 13b, depicting the co-localization of the zinc-charged peptide with the mitochondria marker.
Figure 13D:
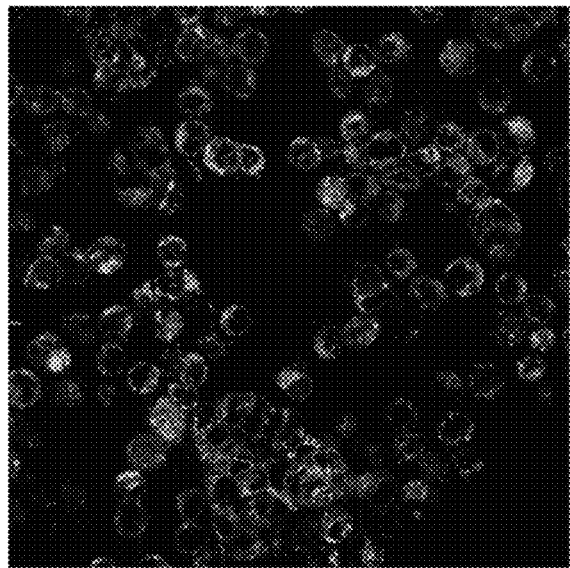
FIG. 13d is a slide depicting the location of the zinc-charged peptide in HT-29 cancer cells by staining the zinc-charged peptide with a fluorescence dye marker.
Figure 13E:
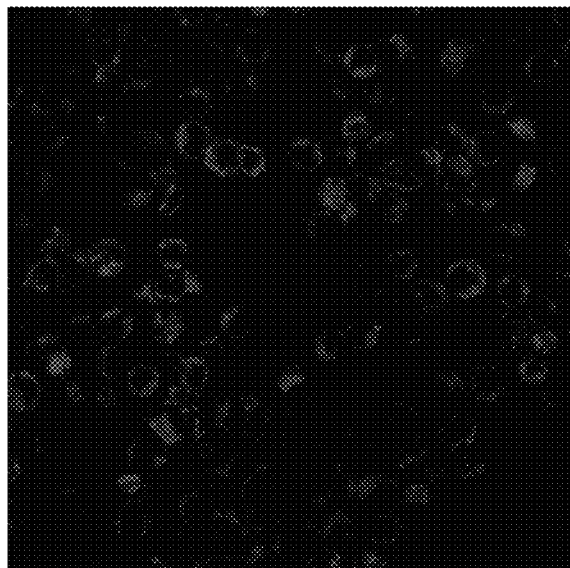
FIG. 13e is a slide depicting the location of the endoplasmic reticulum in HT-29 cancer cells by staining the endoplasmic reticulum with a fluorescence dye marker.
Figure 13F:
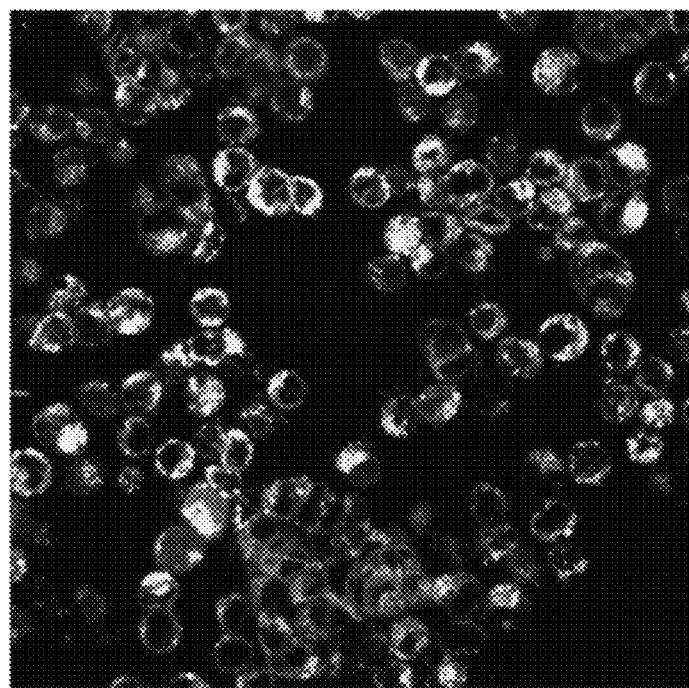
FIG. 13f is a slide depicting the overlapped composite of FIGS. 13d and 13e, depicting the co-localization of the zinc-charged peptide with the endoplasmic reticulum marker.

To trace the location of the zinc-charged peptides once it entered a cell, zinc-charged 4H3 was tagged with FluoZn-3, a zinc-binding fluorescence dye, and was then incubated with HT-29 cells. The cells were then separately stained with either Mito-tracker, the fluorescence dye for mitochondria, or ER-tracker, the fluorescence dye for endoplasmic reticulum. The results of this test can be seen at FIGS. 13a-f. For ease of reference, FIGS. 13a and 13d depict the cell with the zinc-charged 4H3 tagged with FluoZn-3. FIGS. 13b and 13e depict the cells either stained with the Mito-tracker (FIG. 13b) or stained with the ER-tracker (FIG. 13e). FIGS. 13c and 13f are the overlapped composite image of the previous two figures respectively. FIG. 13c is an overlapped composite of FIGS. 13a and 13b, while FIG. 13f is an overlapped composite of FIGS. 13d and 13e.

As shown in FIG. 13, the FluoZn-3 dye images were perfectly superimposed with the Mito-tracker and ER-tracker images, showing full co-localization of the zinc-charged peptides with both the mitochondria marker and the endoplasmic reticulum marker. These results show that after entering cells, the zinc-charged peptides are localized at the mitochondria and endoplasmic reticulum of a cell.

Figure 21:
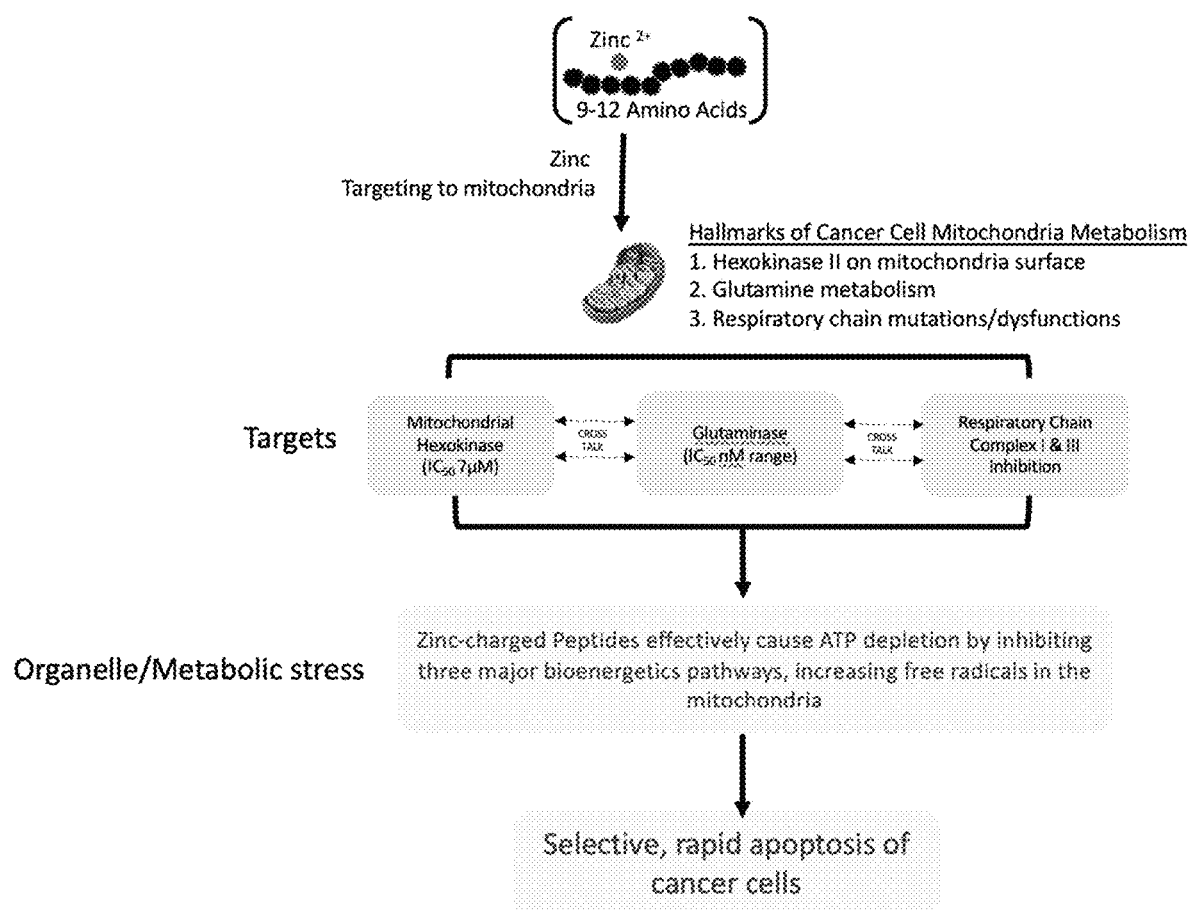
FIG. 21 is a flow diagram providing the overview of the mechanism of action for the zinc-charged peptide inducing rapid apoptosis in cancer cells.

Based on the above testing, the mechanism of action of the zinc-charged peptides was further studied. After it was found that the zinc-charged peptides localized at mitochondria once it enters cells, it was observed that the zinc-charged peptides inhibited three major bioenergetic pathways in mitochondria: (1) hexokinase II, leading to the inhibition of glycolysis, (2) glutaminase, another ATP generation pathway, and (3) respiratory chains I & III, which also generate ATP. A general flow diagraph showing this mechanism of action is presented as FIG. 21.

It is known that hexokinase II presents in cytosol in normal cells, whereas, in cancer cells hexokinase II migrates to mitochondria. Since the zinc-charged peptides localized at the mitochondria, the zinc-charged peptides will inhibit hexokinase II in mitochondria without affecting the hexokinase II in cytosol. This mechanism allows the zinc-charged peptides to selectivity inhibit glycolysis in cancer cells without also inhibiting glycolysis in normal cells. It was also found that the zinc-charged peptides selectively inhibit respiratory chain I & III in cancer with little effect on those normal cells. Lastly, it was also observed that the zinc-charged peptides inhibited glutaminase activity in HT-29 cancer cells and CAFs. The inhibition of these three bioenergy pathways caused the depletion of ATP in cancer cells, leading to the rapid apoptosis in cancer and its microenvironment CAFs.

Figure 14:
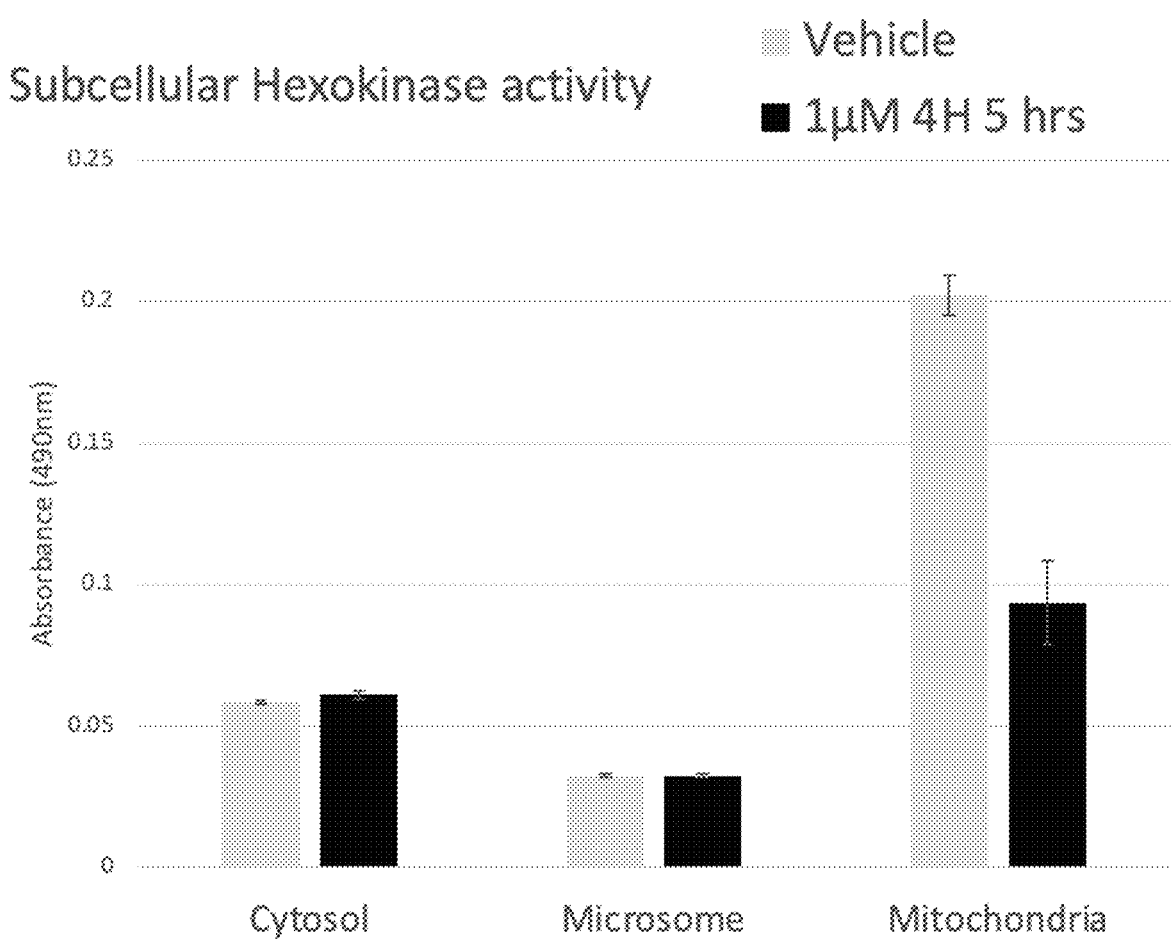
FIG. 14 is a bar graph depicting the subcellular hexokinase II activity in mitochondria, cytosol, and microsome of HT-29 cells incubated with the zinc-charged peptide (4H, 1 µM, for 5 hours) compared to a control of only the vehicle.
Figure 15A:
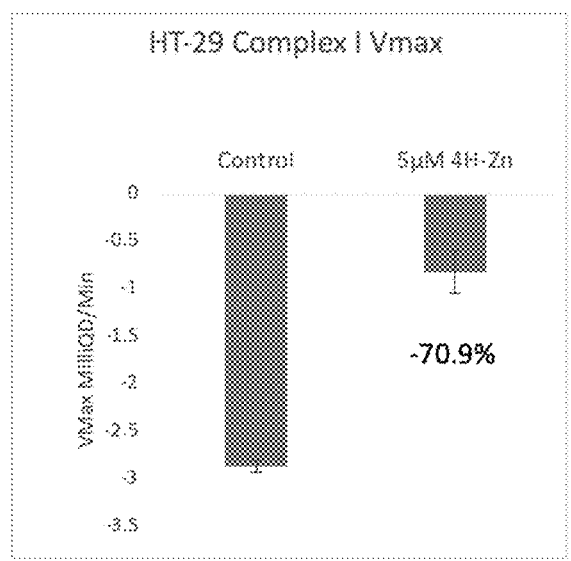
FIG. 15a is a bar graph depicting the inhibition of electron transport in respiratory chain I of mitochondria of HT-29 cancer cells that have been treated with the zinc-charged peptide (4H3, 5 µM, for 2 hours) compared with an untreated control.
Figure 15B:
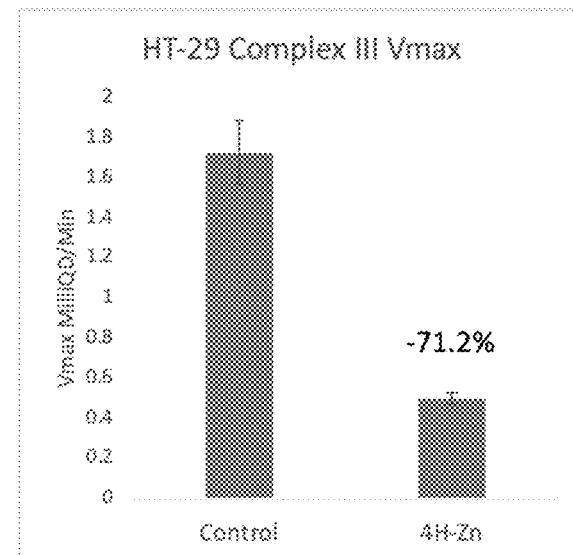
FIG. 15b is a bar graph depicting the inhibition of electron transport in respiratory chain III of mitochondria of HT-29 cancer cells that have been treated with the zinc-charged peptide (4H3, 5 µM, for 2 hours) compared with an untreated control.
Figure 15C:
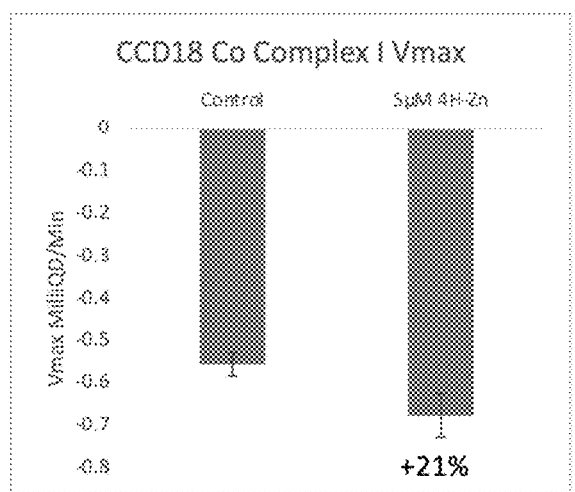
FIG. 15c is a bar graph depicting the increase of electron transport in respiratory chain I of mitochondria of CCD18Co normal colon cells that have been treated with the zinc-charged peptide (4H3, 5 µM, for 2 hours) compared with an untreated control.
Figure 15D:
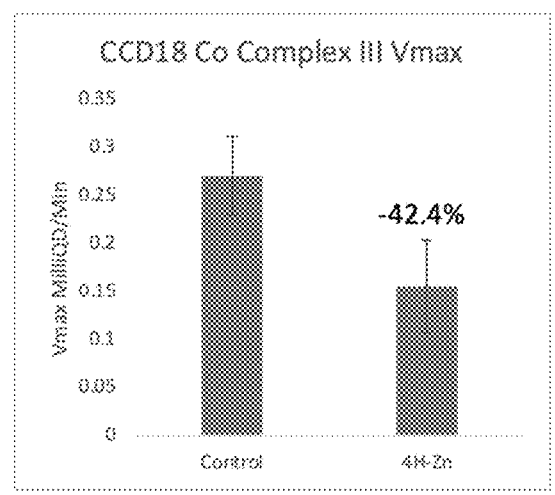
FIG. 15d is a bar graph depicting the decrease of electron transport in respiratory chain III of mitochondria of CCD18Co normal colon cells that have been treated with the zinc-charged peptide (4H3, 5 µM, for 2 hours) compared with an untreated control.

FIGS. 14-16 depicts the testing results validating that the zinc-charged peptides inhibit each of these three bioenergetic pathways. FIG. 14 depicts the subcellular hexokinase II activity in mitochondria, cytosol, and microsome to determine whether the zinc-charged peptides inhibit the hexokinase II activity in mitochondria. For this test, HT-29 cancer cells were incubated with zinc-charged 4H at 1 µM for 5 hours. After incubation, sub-cellular fractions including cytosol, microsome, and mitochondria were prepared and the hexokinase II activity on these sub-cellular fractions were tested. As shown in FIG. 14, most of the hexokinase II activity was found in mitochondria, and importantly, the mitochondria associated hexokinase II activity was inhibited by 53% by zinc-charged 4H.

This result shows that the zinc-charged peptides may selectively inhibit glycolysis in cancer cells but spare the normal ones, as the zinc-charged peptides localized at mitochondria as shown above. The localization of the zinc-charged peptides in the mitochondria is essential as a cancer cell's hexokinase II is present in mitochondria, whereas normal cell's hexokinase II is present in cytosol. This result further confirmed the findings of FIG. 8 showing that zinc-charged 4H has less impact on normal cells' glycolysis than on cancer cells' glycolysis.

FIGS. 15a-d depict the zinc-charged peptide inhibiting respiratory chains I & III in isolated mitochondria. As the most important biological function of mitochondria is its activity on generation of ATP through its respiratory chains, and since the zinc-charged peptides were found to be localized in mitochondria after entering cells, the effects of the zinc-charged peptides were tested on these respiratory chains.

For the testing depicted in FIGS. 15a-15d, 504 zinc-charged 4H3 was utilized and compared to a control. In this test, mitochondria was isolated from the cell line, and complex I and III activity was tested using a Cayman Mitocheck Complex I & III Activity Kit. After the testing was completed, it was found that zinc-charged 4H3 inhibited respiratory chain I by 70.9% and respiratory chain III by 71.2% in HT-29 colon cancer cells. However, the zinc-charged 4H3 increased the activity of respiratory chain I by 21% but inhibited respiratory chain III by 42% in normal CCD8Co colon cells. These results further explain the findings depicted in FIGS. 5 and 10, namely, how the zinc-charged peptides lowered ATP levels by 69.6% in cancer cells but increased the ATP level in normal mice brain by 31.4%.

Figure 16A:
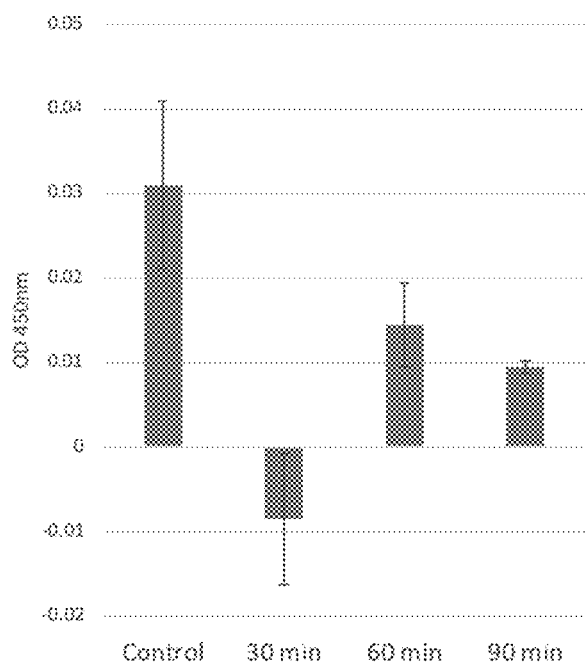
FIG. 16a is a bar graph depicting the inhibition of glutaminase activity in HT-29 cancer cells after incubation with the zinc-charged peptide (4H3, 2 µM) compared to a control.
Figure 16B:
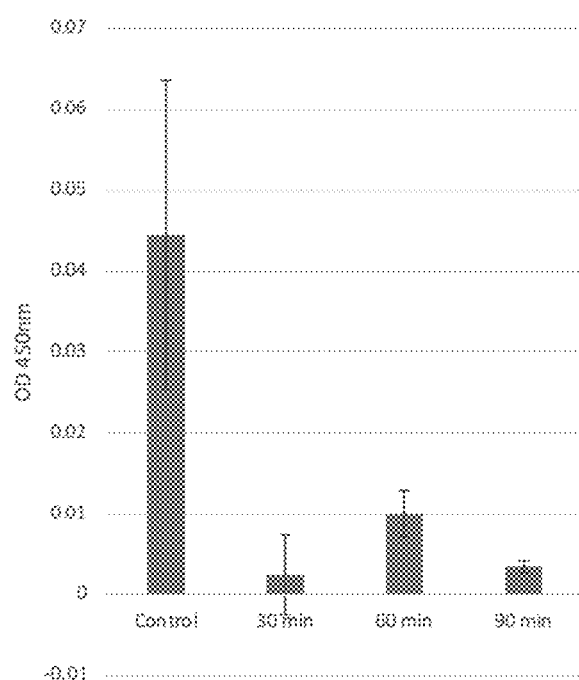
FIG. 16b is a bar graph depicting the decrease of alpha-ketoglutarate in HT-29 cancer cells after incubation with the zinc-charged peptide (4H3, 2 µM) compared to a control.

FIGS. 16a-b depict the zinc-charged peptides inhibiting glutaminase activity in HT-29 cancer cells. Glutaminase is another important enzyme responsible for the synthesis of ATP in mitochondria. It was found that HT-29 cancer cells, after being incubated with 2 µM zinc-charged 4H3 for 30-90 minutes have a lower amount of glutamate and alpha-ketoglutarate, showing a significantly lower glutaminase activity in the cell lysate, as shown in FIGS. 16a and 16b. The inhibition of the enzyme glutaminase, along with the inhibition of respiratory chains in cancer cells explain the depletion of ATP in cancer cells shown in FIG. 5.

It was also determined that the zinc-charged peptides inhibited genes for energy metabolism and mitochondria disruption in cancer cells. On the gene expression level, using gene chip technology, it was found that the zinc-charged peptides inhibit several genes on energy metabolism, such as the genes for cytosol metabolic enzyme (ACLY), mitochondria metabolic enzymes (IDH2 & GPD2) and transcription factor for respiratory chain (NRF1), mitochondria membrane polarization (UCP2), mitochondria protective protein (PINK1), and genes for autophage (ATG5, ATG7, BECN1).

Figure 22:
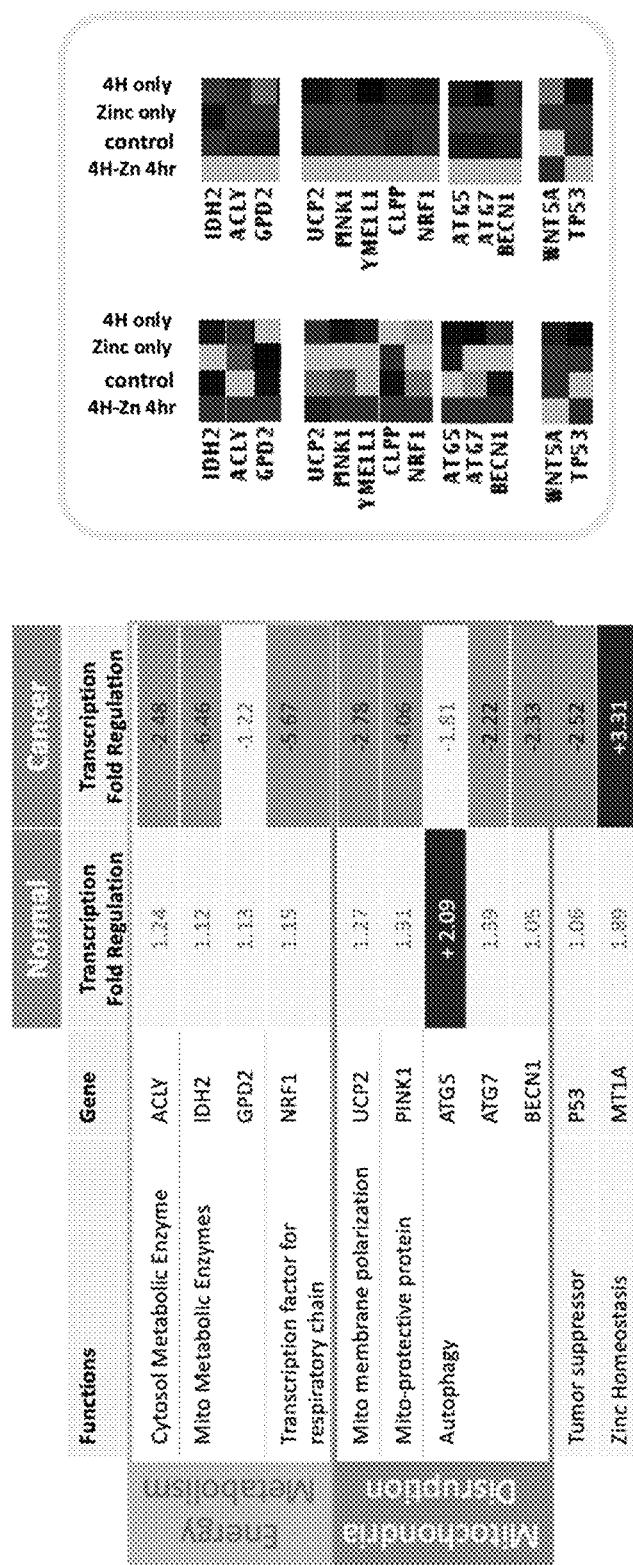
FIG. 22 is a table depicting the gene expression in normal and cancer cells that have been treated with the zinc-charged peptide.

A particularly interesting finding in this study is that the zinc-charged peptides inhibited the expression of these gene in cancer but not in normal cells. As shown in FIG. 22, the zinc-charged peptides inhibited the ATG5 gene in cancer by up to 81% but activated this gene by 109% in normal cells. ATG5 is an important gene for autophage, a cell function for rejuvenation of cell. In this regard, the zinc-charged peptides seem to be able to cause damage in cancer cells but aid normal cells in rejuvenation.

In summation, zinc-charged 4H/4H3 are zinc-charged peptides with 11 amino acid that target mitochondria once they enter cells. These zinc-charged peptides take advantage of the fact that the first enzyme of glycolysis, hexokinase II, which normally present in cytosol for normal cells, migrates to mitochondria in cancer cells. This is why the zinc-charged peptides are able to selectively inhibited hexokinase II in cancer without affecting normal cells.

These zinc-charged peptides also inhibit respiratory chains I and III in mitochondria of cancer cells with less effects on those of normal cells. These zinc-charged peptides also inhibit glutamine metabolism in cancer cells. The inhibition of these three major bioenergetics pathways in mitochondria caused severe ATP depletion in cancer cells resulting in a rapid apoptosis in cancer cells and the CAFs. Each of these findings confirm the first observations from the human tests shown in FIGS. 1-2. Therefore, the zinc-charged peptides can be used as an anti-pancreatic cancer drug, a treatment for various cancers, as well as used as a combination agent for cancer combination therapy.

Biological Activities of the Zinc-Charged Peptides on Diseases Involving Tauopathy Beyond the ability of the zinc-charged peptides to treat cancer and especially pancreatic cancer, pharmacodynamic studies further found that the zinc-charged peptides not only reduced tumor size in mice, but also reduced Tau protein, increased ATP levels in mice brain, and inhibited p38 mitogen-activated protein kinases ("P38 MAPK"). These findings show that the zinc-charged peptides are also capable of treating diseases involving tauopathy such as Alzheimer's Disease and Parkinson's Disease.

During the study of the effect of the zinc-charged peptides on mice brain, it was observed that in mice fed with zinc-charged 4H3 at 1 mg/day for 5 days, the Tau protein in the brain was reduced by 22.4-27.5%, while ATP was increased by 89.9% and P38 MAPK reduced by 61%.

Figure 11A:
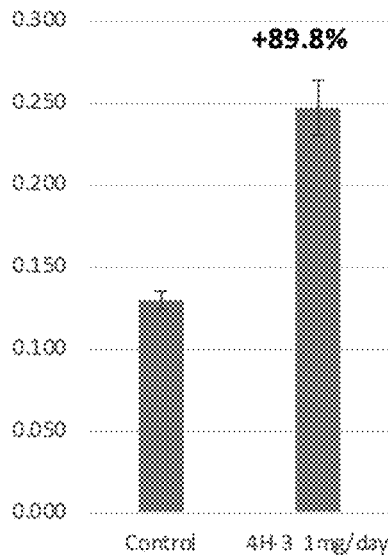
FIG. 11a is a bar graph depicting the brain ATP level of mice after the mice were orally administered the zinc-charged peptide (4H3, 1 mg/mouse) for five days compared to a control.
Figure 11B:
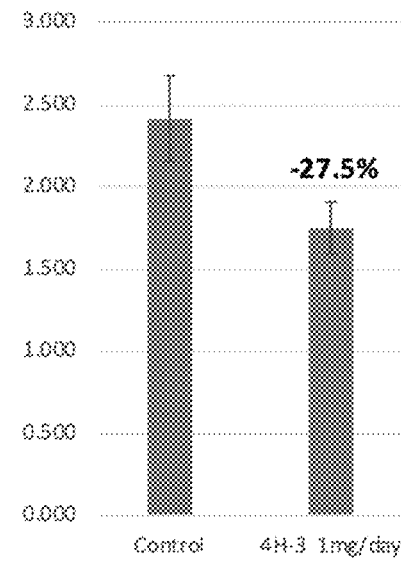
FIG. 11b is a bar graph depicting the brain Tau protein levels of mice orally administered the zinc-charted peptide (4H3, 1 mg/mouse) for five days compared to a control. ELISA was used for Tau protein quantification (2.7 µg protein load).
Figure 11C:
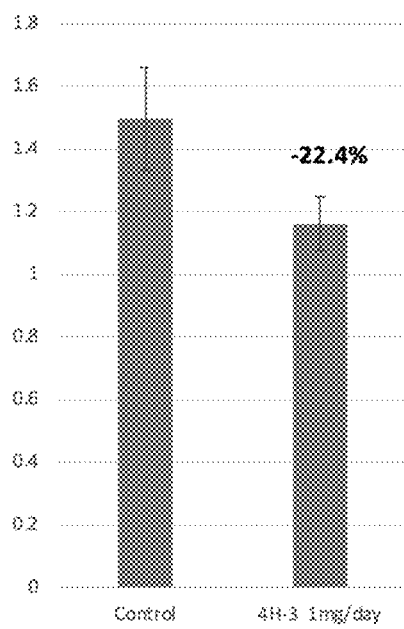
FIG. 11c is a bar graph depicting the brain Tau protein levels of mice orally administered the zinc-charted peptide (4H3, 1 mg/mouse) for five days compared to a control. ELISA was used for Tau protein quantification (0.55 µg protein load).
Figure 11D:
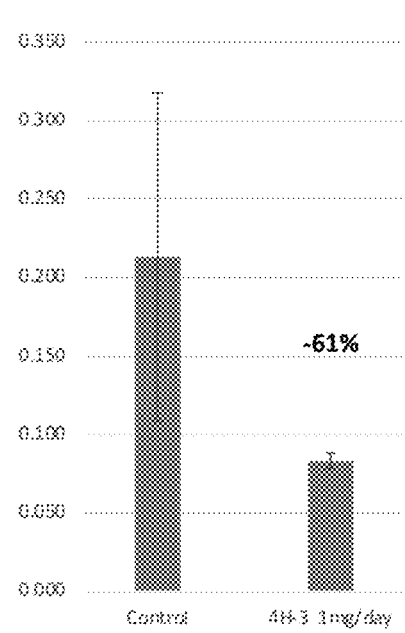
FIG. 11d is a bar graph depicting the brain P38 MAPK level of mice after the mice were administered the zinc-charged peptide (4H3, 1 mg/mouse) for five days compared to a control.

FIGS. 11a-d provide the graphical representations of these observations. FIG. 11a depicts the level of brain ATP in mice that were orally administered zinc-charged 4H3 compared to mice who were given the control. In this test, the mice given the zinc-charged 4H3 saw their brain ATP levels increase by 89.8%. FIG. 11b depicts the level of brain Tau protein ATP in mice that were orally administered zinc-charged 4H3 compared to mice who were given the control. In this test, a 2.7 μg protein load was utilized. This test showed a 27.5% decrease in the Tau protein in mice who were given the zinc-charged 4H3 compared to the control. FIG. 11c depicts a retest of FIG. 11b, but with a lower protein load utilized instead. For the test depicted in FIG. 11c, a 0.55 μg protein load was utilized, resulting in a 22.4% decrease in Tau protein in mice given the zinc-charged 4H3 compared to the control. Lastly, FIG. 11d depicts the brain P38 MAPK levels in mice that were orally administered zinc-charged 4H3 compared to mice who were given the control. In this test, the mice given the zinc-charged 4H3 saw their brain P38 MAPK levels decrease by 61%.

Tau protein has been reported to be involved in neurodegenerative diseases such as Alzheimer's Disease and Parkinson's Disease. Furthermore, the ATP level in the brain of Alzheimer's patients has been found to be lower than normal. P38 MAPK was found to involved in the pathogenesis of Alzheimer's disease and inhibition of P38 MAPK improved memory impairment in an Alzheimer's Disease mouse model. On a gene expression level, there is an emerging agreement that defects in autophage such as ATG5 likely contribute to the neurodegenerative processes in numerous diseases, including Alzheimer's Disease.

Therefore, as thoroughly discussed above, the zinc-charged peptides have been shown to (1) increase ATP in the brain, (2) lower Tau protein in the brain, (3) inhibit P38 MAPK in the brain, and (4) enhance autophage by enhancing ATG5 gene expression. All these results demonstrate that the zinc-charged peptides can treat Alzheimer's Disease and other diseases involving tauopathy.

Method of Treating Cancer Using the Zinc-Charged Peptides

As it has been established that the zinc-charged peptide induces apoptosis in cancer cells, an in vivo method of treating cancer utilizing the zinc-charged peptide is also disclosed. The method of treating cancer includes administering an effective amount of a zinc-charged peptide to a patient in need thereof. The zinc-charged peptide may be administered orally, or by any other suitable means of administration. The zinc-charged peptide may be administered in its liquid form or in its dry, solid form. The zinc-charged peptide may be either zinc-charged 4H or zinc-charged 4H3.

An in vitro method of inducing apoptosis in cancer cells is also provided. This method includes administering a zinc-charged peptide to the cancer cells. The zinc-charged peptide may be either zinc-charged 4H or zinc-charged 4H3 and may be in their solid or liquid form.

Method of Treating Diseases Involving Tauopathy Using the Zinc-Charged Peptides

As it has been established that the zinc-charged peptide also lowers Tau protein levels and increases ATP levels in the brain, an in vivo method of treating diseases involving tauopathy, such as Alzheimer's Disease and Parkinson's Disease, utilizing the zinc-charged peptide is also disclosed. The method of treating diseases involving tauopathy include administering an effective amount of a zinc-charged peptide to a patient in need thereof. The zinc-charged peptide may be administered orally, or by any other suitable means of administration. The zinc-charged peptide may be administered in its liquid form or in its dry, solid form. The zinc-charged peptide may be either zinc-charged 4H or zinc-charged 4H3.

An in vitro and in vivo method of reducing Tau proteins and increasing ATP in the brain is also provided. This method includes administering a zinc-charged peptide to the brain. The zinc-charged peptide may be either zinc-charged 4H or zinc-charged 4H3 and may be in their solid or liquid form.

I claim:

1. A composition for inducing apoptosis in cancer cells of a patient, the composition comprising:
    a zinc-charged peptide,
    wherein said zinc-charged peptide comprises an amino acid sequence chosen from the the amino acid sequence shown in SEQ. NO. 2.

2. An in vivo method of inducing apoptosis in cancer cells of a patient, the method comprising:
    administering a zinc-charged peptide to said patient;
    wherein the zinc-charged peptide comprises an amino acid sequence chosen from the amino acid sequence shown in SEQ. NO. 2.

3. The method of claim 2 wherein the zinc-charged peptide is administered to the patient orally.

4. A method of preparing a zinc-charged peptide, the method comprising:
    (1) preparing a peptide;
    (2) dissolving said peptide in a solvent;
    (3) incubating the dissolved peptide with a chelating agent; and
    (4) incubating the resulting mixture from step (3) with an excess of a zinc compound;
    wherein the peptide is charged with zinc ions from the zinc compound, resulting in a zinc-charged peptide; and
    wherein the prepared zinc-charged peptide has an amino acid sequence chosen from the amino acid sequence shown in SEQ. NO. 2.

5. The method of claim 4 further comprising the step of (5) separating the zinc-charged peptide from the mixture resulting from step (4).

6. The method of claim 5 further comprising the step of (6) drying the zinc-charged peptide.

7. The method of claim 4 wherein the chelating agent is ethylenediaminetetraacetic acid.

8. The method of claim 4 wherein the zinc compound is zinc acetate.

9. The method of claim 8 wherein the excess of the zinc acetate is 50 mM of the zinc acetate.

10. The method of claim 4, wherein the excess of the zinc compound is 50 mM of the zinc compound.

* * * * *

SEQUENCE LISTING

<160> NUMBER OF SEQ ID NOS: 2

<210> SEQ ID NO 1
<211> LENGTH: 11

```
<212> TYPE: PRT
<213> ORGANISM: Artificial Sequence
<220> FEATURE:
<223> OTHER INFORMATION: chemically synthesized peptide based upon the
      amino acid sequence of alpha-lactalbumin

<400> SEQUENCE: 1

Glu Tyr Gly Leu Phe Gln Ile Ser Asn Lys Leu
1               5                   10

<210> SEQ ID NO 2
<211> LENGTH: 11
<212> TYPE: PRT
<213> ORGANISM: Artificial Sequence
<220> FEATURE:
<223> OTHER INFORMATION: chemically synthesized peptide based upon the
      amino acid sequence of alpha-lactalbumin

<400> SEQUENCE: 2

Glu Tyr Gly Leu Phe Gln Ile Ser Asn Lys Lys
1               5                   10
```